United States Patent [19]

Rosenberg et al.

[11] Patent Number: 4,857,507
[45] Date of Patent: * Aug. 15, 1989

[54] ANGIOTENSINOGEN ANALOGS

[75] Inventors: Saul H. Rosenberg, Libertyville; Joseph Dellaria, Lindenhurst; Anthony K. L. Fung, Waukegan; Dale J. Kempf, Lake Villa; Jay R. Luly; Jacob J. Plattner, both of Libertyville, all of Ill.

[73] Assignee: Abbott Laboratories, Abbott Park, Ill.

[*] Notice: The portion of the term of this patent subsequent to Feb. 24, 2004 has been disclaimed.

[21] Appl. No.: 946,883

[22] Filed: Jan. 9, 1987

Related U.S. Application Data

[63] Continuation-in-part of Ser. No. 850,802, Apr. 11, 1986, which is a continuation-in-part of Ser. No. 820,274, Jan. 16, 1986.

[51] Int. Cl.[4] .............. A61K 37/43; C07K 5/08; C07K 5/10
[52] U.S. Cl. .................. 514/18; 530/330; 530/331
[58] Field of Search .................. 514/17; 530/331, 330

[56] References Cited

U.S. PATENT DOCUMENTS 4,645,759 2/1987 Luly et al. .................. 530/331

OTHER PUBLICATIONS

Biochemical and Biophysical Research Communication 132 No. 1 (1985), 155-161.
Chem. Abstr. vol. 105 (1986) 209389.
Chem. Abstr. vol. 85 (1976) 1676s.
Chem. Abstr. vol. 103 (1985) 50255c.
Chem. Abstr. vol. 103 (1985) 142365.
Chem. Abstr. vol. 103 (1985) 142380.

*Primary Examiner*—Delbert R. Phillips
*Attorney, Agent, or Firm*—Michael J. Roth; Steven F. Weinstock; Martin L. Katz

[57] ABSTRACT

The invention relates to renin inhibiting compounds of the formula

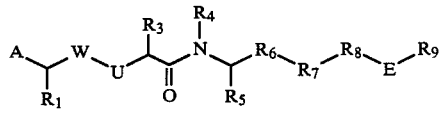

wherein A is hydrogen; loweralkyl; arylalkyl; $OR_{10}$ or $SR_{10}$ wherein $R_{10}$ is hydrogen, loweralkyl or aminoalkyl; $NR_{11}R_{12}$ wherein $R_{11}$ and $R_{12}$ are independently selected from hydrogen, loweralkyl, aminoalkyl, cyanoalkyl and hydroxyalkyl;

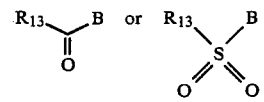

wherein B is NH, alkylamino, S, O, $CH_2$ or CHOH and $R_{13}$ is loweralkyl, cycloalkyl, aryl, arylalkyl, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, (dihydroxyalkyl)(alkyl)amino, aminoalkyl, alkoxycarbonylalkyl, carboxyalkyl, N-protected aminoalkyl, alkylaminoalkyl, (N-protected)(alkyl)aminoalkyl, dialkylaminoalkyl, (heterocyclic) alkyl or a substituted or unsubstituted heterocyclic; W is CO or CHOH and U is $CH_2$ or $NR_2$ with the proviso that when W is CHOH then U is $CH_2$; $R_1$ is loweralkyl, cycloaklylmethyl, benzyl, $\alpha,\alpha$-dimethylbenzyl, 4-methoxybenzyl, halobenzyl, (1-naphthyl)-methyl, (2-naphthyl)methyl, (4-imidazoyl)-methyl, phenethyl, phenoxy, thiophenoxy or anilino; provided if $R_1$ is phenoxy, thiophenoxy or anilino, B is $CH_2$ or CHOH or A is hydrogen, $R_3$ is loweralkyl, vinyllower-alkyl, benzyl or heterocyclic ring substituted methyl, $R_5$ is loweralkyl, cycloalkylmethyl or benzyl; $R_2$ and $R_4$ are independently selected from hydrogen and loweralkyl; $R_6$ is CHOH or CO; $R_7$ is $CH_2$, $CF_2$ or CF with the proviso that when $R_6$ is CO, $R_7$ is $CF_2$; $R_8$ is $CH_2$, $CHR_{14}$ wherein $R_{14}$ is lower-alkyl, cycloalkyl, cycloalkylalkyl, aryl or arylalkyl, or $R_7$ and $R_8$ taken together can be

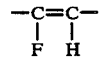

with the proviso that when $R_7$ is $CF_2$, $R_8$ is $CH_2$; E is O, S, SO, $SO_2$, $NR_{15}$ wherein $R_{15}$ is hydrogen or loweralkyl or $NR_{16}CO$ wherein $R_{16}$ is hydrogen or loweralkyl; $R_9$ is loweralkyl, cycloalkyl, cycloalkylalkyl, aryl, arylalkyl or an N-protected group, or E and $R_9$ taken together can be $N_3$, with the proviso that when E is NH, $R_9$ is an N-protecting group; and pharmaceutically acceptable salts thereof.

14 Claims, No Drawings

ANGIOTENSINOGEN ANALOGS

TECHNICAL FIELD

This application is a continuation-in-part of application Ser. No. 06/850,802 filed Apr. 11, 1986, which is a continuation-in-part of application Ser. No. 06/820,274 filed Jan. 16, 1986.

The present invention relates to novel organic compounds which inhibit renin.

BACKGROUND ART

Renin is a proteolytic enzyme synthesized and stored principally in a specific part of the kidney called the juxtaglomerular apparatus. Any of three different physiologic circumstances may cause the release of renin into the circulation: (a) a decrease in the blood pressure entering or within the kidney itself; (b) a decrease in the blood volume in the body; or (c) a fall in the concentration of sodium in the distal tubules of the kidney.

When renin is released into the blood from the kidney, the renin-angiotensin system is activated, leading to vasoconstriction and conservation of sodium, both of which result in increased blood pressure. The renin acts on a circulating protein, angiotensinogen, to ceave out a fragment called angiotensin I (AI). AI itself has only slight pharmacologic activity but, after additional cleavage by a second enzyme, angiotensin converting enzyme (ACE), forms the potent molecule angiotensin II (AII). The major pharmacological effects of AII are vasoconstriction and stimulation of the adrenal cortex to release aldosterone, a hormone which causes sodium retention. AII is cleaved by an aminopeptidase to form angiotensin II (AIII), which, compared to AII, is a less potent vasoconstrictor but a more potent inducer of aldosterone release.

Inhibitors of renin have been sought as agents for control of hypertension and as diagnostic agents for identification of cases of hypertension due to renin excess.

With these objectives in mind, the renin-angiotension system has been modulated or manipulated, in the past, with ACE inhibitors. However, ACE acts on several substrates other than angiotensin I (AI), most notably the kinins which cause such undesirable side effects as pain, "leaky" capillaries, prostaglandin release and a variety of behavioral and neurologic effects. Further, ACE inhibition leads to the accumulation of AI. Although AI has much less vasoconstrictor activity than AII, its presence may negate some of the hypotensive effects of the blockade of AII synthesis.

Inhibition of other targets in the renin-angiotensin system such as AII with compounds such as saralasin can block AII activity, but would leave unimpaired and perhaps enhance the hypertensive effects of AIII.

On the other hand, there are no known side effects which result when renin is inhibited from acting on its substrate. Considerable research efforts have thus been carried out to develop useful inhibitors of renin. Past research efforts have been directed to renin antibodies, pepstatin, phospholipids and substrate analogs such as tetrapeptides and octapeptides to tridecapeptides. These inhibitors either demonstrate poor activity in inhibiting renin production or poor specificity for inhibiting renin only. However, Boger et al. have reported that statine-containing peptides possess potent and specific renin-inhibiting activity (*Nature,* Vol. 303, p. 81, 1983). In addition, Szelke and co-workers have described polypeptide analogs containing a non-peptide link (*Nature,* Vol. 299, p. 555, 1982) which also cause potent renin inhibition and show a high specificity for this enzyme.

DISCLOSURE OF THE INVENTION

In accordance with the present invention, there are renin inhibiting compounds of the formula

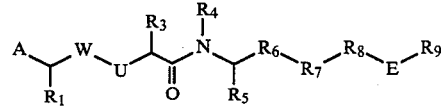

wherein A is hydrogen; loweralkyl; arylalkyl; $OR_{10}$ or $SR_{10}$ wherein $R_{10}$ is hydrogen, loweralkyl or aminoalkyl; $NR_{11}R_{12}$ wherein $R_{11}$ and $R_{12}$ are independently selected from hydrogen, loweralkyl, aminoalkyl, cyanoalkyl and hydroxyalkyl;

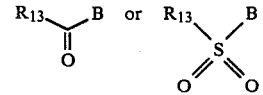

wherein B is NH, alkylamino, S, O, $CH_2$ or CHOH and $R_{13}$ is loweralkyl, cycloalkyl, aryl, arylalkyl, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, (dihydroxyalkyl) (alkyl)amino, aminoalkyl, alkoxycarbonalkyl, carboxyalkyl, N-protected aminoalkyl, alkylaminoalkyl, (N-protected)(alkyl)aminoalky, dialkylaminoalkyl, (heterocyclic)alkyl or a substituted or unsubstituted heterocyclic; W is C or CHOH and U is $CH_2$ or $NR_2$ with the proviso that when W is CHOH then U is $CH_2$; $R_1$ is loweralkyl, cycloalkylmethyl, benzyl, α, α-dimethylbenzyl, 4-methoxybenzyl, halobenzyl, (1-naphthyl)methyl, (2-naphthyl)methyl, (4-imidazolyl)methyl, phenethyl, phenoxy, thiophenoxy or anilino, B is $CH_2$ or CHOH or A is hydrogen; $R_3$ is loweralkyl, vinylloweralkyl, benzyl or heterocyclic ring-substituted methyl; $R_5$ is loweralkyl, cycloalkylmethyl or benzyl; $R_2$ and $R_4$ are independently selected from hydrogen and loweralkyl; $R_6$ is CHOH or CO; $R_7$ is $CH_2$, $CF_2$ or CF with the proviso that when $R_6$ is CO, $R_7$ is $CF_2$; $R_8$ is $CH_2$, $CHR_{14}$ wherein $R_{14}$ is lower-alkyl, cycloalkyl, cycloalkylalkyl, aryl or arylalkyl, or $R_7$ and $R_8$ taken together can be

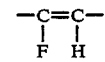

with the proviso that when $R_7$ is $CF_2$, $R_8$ is $CH_2$; E is O, S, SO, $SO_2$, $NR_{15}$ wherein $R_{15}$ is hydrogen or loweralkyl or $NR_{16}CO$ wherein $R_{16}$ is hydrogen or loweralkyl; $R_9$ is loweralkyl, cycloalkyl, cycloalkylalkyl, aryl, arylalkyl or an N-protected group, or E and $R_9$ taken together can be $N_3$, with the proviso that when E is NH, $R_9$ is an N-protecting group; and pharmaceutically acceptable salts thereof.

The preferable compounds are when $R_2$ and $R_4$ are hydrogen, $R_1$ is benzyl, 1- or 2-naphthylmethyl and $R_5$ is cyclohexylmethyl. The most preferable compounds are when $R_3$ is isobutyl or imidazol-4-yl-methyl, $R_6$ is CO, $R_7$ is $CF_2$, $R_8$ is $CH_2$ and E is S or $SO_2$.

The chiral centers of the compounds of the invention may have either the "R" or "S" configuration but preferably have an "S" configuration.

The term "loweralkyl" as used herein refers to straight or branched chain alkyl radicals containing from 1 to 6 carbon atoms including but not limited to methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

the term "aminoalkyl" as used herein refers to —$NH_2$ appended to a loweralkyl radical.

The term "cyanoalkyl" as used herein refers to —CN appended to a loweralkyl radical.

The term "cycloalkyl" as used herein refers to an alicyclic residue and includes but is not limited to cyclohexyl and cyclopentyl.

The term "cycloalkylalkyl" as used herein refers to an alicyclic residue appended to an alkyl radical and includes but is not limited to cyclohexylmethyl and cyclopentylmethyl.

The term "aryl" as used herein refers to an unsubstituted or substituted aromatic ring including but not limited to phenyl, halophenyl, loweralkylphenyl, naphthyl and heteroaryl.

The terms "alkoxy" and "thioalkoxy" as used herein refer to $R_{17}O$— and $R_{17}S$—, respectively, wherein $r_{17}$ is a loweralkyl group.

The term "alkenyloxy" as used herein refers to $R_{18}O$— wherein $R_{18}$ is an unsaturated alkyl group.

The term "hydroxyalkoxy" as used herein refers to an alkoxy radical which is disubstituted with —OH radicals.

The term "arylalkoxy" as used herein refers to an aryl appended to an alkoxy radical.

The term "arylalkoxyalkyl" as used herein refers to an aryalkoxy appended to a loweralkyl radical.

The term "(thioalkoxy)alkyl" as used herein refers to thioalkoxy appended to a loweralkyl radical.

The term "dialkylamino" as used herein refers to —$NR_{19}R_{20}$ wherein $R_{19}$ and $R_{20}$ are independently selected from loweralkyl groups.

The term "dialkylaminoalkyl" as used herein refers to a dialkylamino appended to a loweralkyl radical.

The term "[(alkoxy)alkoxy]alkyl" refers to an alkoxy group appended to an alkoxy group which is appended to a loweralkyl radical.

The term "hydroxyalkyl" as used herein refers to —OH appended to a loweralkyl radical.

The term "(hydroxyalkyl)(alkyl)amino" as used herein refers to —$NR_{21}R_{22}$ wherein $R_{21}$ is hydroxyalkyl and $R_{22}$ is loweralkyl.

The term "N-protecting group" as used herein refers to those groups intended to protect the N-terminus against undesirable reactions during synthetic procedures or to prevent the attack of exopeptidases on the final compounds or to increase the solubility of the final compounds and includes but is not limited to sulfonyl, acyl, acetyl, pivaloyl, t-butyloxycarbonyl(Boc), carbonbenzyloxycarbonyl or benzoyl groups or an L- or D-aminoacyl residue, which may itself be N-protected similarly.

The term "N-protected aminoalkyl" as used herein refers to $NHR_{23}$ appended to a loweralkyl group, wherein $R_{23}$ is an N-protecting group.

The term "alkylaminoalkyl" as used herein refers to $NHR_{24}$ appended to a loweralkyl radical, wherein $r_{24}$ is a loweralkyl group.

The term "(N-protected)(alkyl)aminoalkyl" as used herein refers to $NR_{23}R_{24}$, which is appended to a loweralkyl radical, wherein $R_{23}$ and $R_{24}$ are as defined above.

The term alkoxycarbonylalkyl as used herein refers to $R_{25}COR_{26}$, wherein $R_{25}$ is an alkoxy group and $R_{26}$ is loweralkyl.

The term carboxyalkyl as used herein refers to a carboxylic acid group (—COOH) appended to a loweralkyl radical.

The term "(heterocyclic)alkyl" as used herein refers to a heterocyclic group appended to a loweralkyl radical, including but not limited to imidazolylalkyl.

The term "heterocyclic ring" or "heterocyclic" as used herein refers to any 5-, 6-, 9- or 10-membered ring containing from one to three heteroatoms selected from the group consisting of nitrogen, oxygen, and sulfur; having various degrees of unsaturation; wherein the nitrogen and sulfur heteroatoms may optionally be oxidized; wherein the nitrogen heteroatoms may optionally be quaternized; and including any bicyclic group in which any of the above heterocyclic rings is fused to a benzene ring. Heterocyclics in which nitrogen is the heteroatom are preferred. Fully saturated heterocyclics are also preferred. Preferred heterocyclics are: pyrryl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isthiazolyl, isothiazolidinyl, indolyl, quinolinyl, isoquinolinyl, benzimidazolyl, benzothiazolyl, benzoxazolyl, furyl, thienyl and benzothienyl.

Saturated heterocyclics may be unsubstituted or monosubstituted with hydroxy, oxo, amino, alkylamino, dialkylamino or loweralky. Unsaturated heterocyclics may be unsubstituted or monosubstituted with hydroxy, amino, alkylamino, dialkylamino or loweralkyl.

The most preferred heterocyclics are as follows:

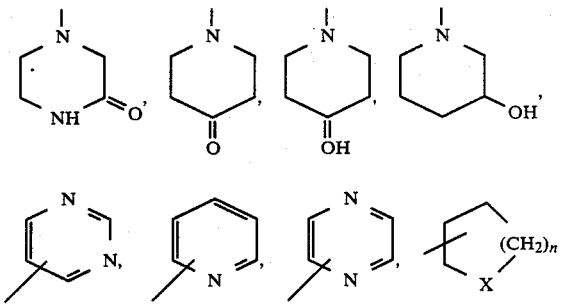

wherein n is 1 or 2 and X is N, NH, O, S, provided that X is the point of connection only when X is N,

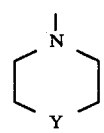

wherein Y is NH, N-loweralkyl, O, S, or $SO_2$, or

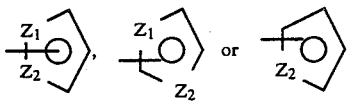

wherein $Z_1$ is N, O, or S and not the point of connection and $Z_2$ is N when it is the point of connection and NH, O or S when it is not the point of connection.

The term "arylalkyl" as used herein refers to an unsubstituted or substituted aromatic ring appended to an alkyl radical including but not limited to benzyl, 1-and 2-naphthylmethyl, halobenzyl and alkoxybenzyl.

The terms "lipophilic or aromatic amino acid side chains" as used herein refers to those amino acid side chains which have an affinity for lipids or have an aromatic ring and include but are not limited to isobutyl, isopropyl, benzyl, imidazole-4-yl-methyl, p-hydroxybenzyl, 1- and 2-naphthylmethyl, (pyrazolyl)methyl, (thiazolyl)methyl, and cyclohexylmethyl. General reference to amino acid side chains in both the description and claims here is to be taken as reference to such, whether naturally occurring in proteins or not, and to both D- and L- forms.

The terms "Ala", "His", "Leu", "Phe", "Tyr", "Cys", "Gly", "Lys", Sar" and "Pro" as used herein refer to alanine, histidine, leucine, phenylalanine, tyrosine, cysteine, glycine, lysine, sarcosine and proline, respectively.

The term "(dihydroxyalkyl)(alkyl)amino" as used herein refers to a loweralkyl group which is disubstituted with -OH radicals appended to an amino group, which amino group also has appended another loweralkyl group.

The following Examples will serve to further illustrate preparation of novel compounds of the present invention.

EXAMPLE 1

(3S,4s)-4-t-Butyloxycarbonylamino-3-hydroxy-6-methyl-l-heptene

To a rapidly stirred −78° C. solution of Box-leucinal (1.5 g, 6.97 mmol) in anhydrous tetrahydrofuran (THF) (10 mL) was added a −78° C. solution of vinyl magnesium bromide (7 mmol) in anhydrous THF (40 mL) dropwise over the course of 15 minutes, and 2 hours later the mixture was acidified to pH 7. The organic phase was separated, washed with brine (2×10 mL) and dried ($Na_2DO_4$). Filtration and evaporation provided an oil which was purified by flash chromatography on silica gel with 7/3 hexane-ether. There was obtained 3.9 (53%) of product, m.p. 15°–59° C.

Anal. calcd. for $D_{13}H_{25}NO_3$: C, 64.17; H, 10,36; N, 5.76. Found: C, 64.19; H, 10.13; N, 5.66.

EXAMPLE 2

4(D)-Isobutyl-5(S)-vinyl-2-oxazolidinone

To a solution of (3S,4S)-4-t-butyloxycarbonylamino-3-hydroxy-6methyl-1-heptene (10.5 g, 0.043 mole) in dimethylformamide (DMF) (100 mL) was added sodium hydride (2.4 g of 50% dispersion) portionwise at 0°–5° C. After stirring for 20 hours at room temperature, the reaction mixture was poured into cold aqueous NaCl solution. The resulting mixture was extracted with methylene chloride and the organic phase was washed several times with brine solution. Drying over $MgSO_4$ and evaporation gave a residue which was flash chromatographed on silica gel eluting with hexane/ethyl acetate mixtures. There was obtained 5.7 g (78%) of the desired compound as an oil. NMR (300 MHz, $CDCl_3$, ppm): 0.9 (2d, 6H), 1.35–1.75 (m, 3H), 3.6 (m, 1H), 4.55 (t, 1H), 5.4 (m, 2H), 5.9 (m, 1H).

EXAMPLE 3

4(S)-Isobutyl-5(S)-(2-mesyloxyethyl)-2-oxazolidinone

To a 0° C. solution of 4(S)-isobutyl-5(S)-vinyl-2-oxazolidinone (4.7 g, 0.028 mole) in THF (20 mL) was added 9-BBN [9-borabicyclo(3.3.1)nonane, 75 mL, 0.0375 mole in THE] by dropwise addition. After stirring for 5 hours at room temperature, the reaction was quenched by the addition of water (1 mL). A solution of NaOH (6.7 g) in water (21 mL) was then added followed by careful addition of $H_2O_2$ (18 mL of 30%). The resulting mixture was heated at 65° C. for 1 hour, the THF was partially evaporated and the residue was distributed between ethyl acetate and brine solution. The organic phase was washed with brine solution and dried over $MgSO_4$. Evaporation of the solvent gave a residual oil which was flash chromatographed on silica gel eluting with 5% MeOH in methylene chloride. The pure fractions were combined and evaporated to give 4.62 g of 4(S)-isobutyl-5(S)-(2-hydroxyethyl)-2-oxazolidinone. A solution of this material (3.95 g, 0.021 mol) and triethylamine (3.2 g, 0.032 mol) in methylene chloride (40 mL) was cooled to 0° C. and treated by dropwise addition with mesyl chloride (2.89 g, 0.025 mol). After stirring for 1 hour at 0–5° C., the methylene chloride was washed successively with 0.5 N HCl, aqueous $NaHCO_3$ and brine solution. The organic solution was dried and evaporated to a solid product. Recrystallization from hexane/methylene chloride gave 3.9 g (70%) of product, m.p. 99°–100° C.

Analysis calculated for $C_{10}H_{19}NO_5S$: C, 45.27; H, 7.22; N, 5.28. Found: C, 45.38; H, 7.18; N, 5.23.

EXAMPLE 4

4(S)-Isobutyl-5(S)-[2-(phenethylmercapto)ethyl]-2-oxazolidinone

To a 0° C. solution of 4(S)-isobutyl-5(S)-(2-mesyloxyethyl)-2-oxazolidinone (500 mg, 1.88 mmol) and phenethyl mercaptan (273 mg, 1.98 mmol) in THF (6 mL) was added NaH (95 mg, 1.98 mmol of a 50% dispersion) all at once. The reaction was stirred for 3 hours at room temperature and then distributed between methylene chloride and brine solution. The organic layer was washed with brine solution, dried over $MgSO_4$ and evaporated. The residue was chromatographed on silica gel eluting with 65/35 hexaneethyl acetate to give 570 mg (98%) of product as an oil.

Analysis calculated for $C_{17}H_{25}NO_2S$: C, 66.41; H, 8.20; N, 4.56. Found: C, 66.60; H, 8.32; N, 4.58.

EXAMPLE 5

4(S)-Isobutyl-5(S)-[2-(isoamylmercapto)ethyl]-2-oxazolidinone

Using the procedure of Example 4 but changing phenethyl mercaptan to isoamyl mercaptan, gave the desired compound in 95% yield.

Analysis calculated for $C_{14}H_{27}NO_2S$: C, 61.50; H, 9.95; N, 5.12. Found: C, 61.19; H, 10.02; N, 5.00.

EXAMPLE 6

4(S)-Isobutyl-5(S)-[2-(isobutylmercapto)ethyl]-2-oxazolidinone

Using the procedure of Example 4 but changing phenethyl mercaptan to isobutyl mercaptan, gave the desired compound in 96% yield.

EXAMPLE 7

4(S)-Isobutyl-5(S)-[2-(isopropylmercapto)ethyl]-2-oxazolidinone

Using the procedure of Example 4 but changing phenethyl mercaptan to isopropyl mercaptan, gave the desired compound in 93% yield.

EXAMPLE 8

4(S)-Isobutyl-5(S)-[2-(phenethylsulfonyl)ethyl]-2-oxazolidinone

To a solution of 4(S)-isbutyl-5(S)-[2-(phenethylmercapto)ethyl]-2-oxazolidinone (0.49 g, 1.59 mmol) in methylene chloride (6 mL) was added 0.756 g (3.5 mmol) of m-chloroperoxybenzoic acid. After stirring for 1 hour at room temperature, the methylene chloride solution was washed successively with aqueous $NaHSO_3$ and aqueous NaOH. The organic layer was dried and evaporated to a solid product. Trituration with hexane/ether (50/50) gave 495 mg (92%) of product, m.p. 100–101° C.

Analysis calculated for $C_{17}H_{25}NO_4S$: C, 60.15; H, 7.42; N, 4.13. Found: C, 60.27; H, 7.42; N, 4.00.

EXAMPLE 9

4(S)-Isobutyl-5(S)-[2-isoamylsulfonyl)ethyl]-2-oxazolidinone

Using the procedure of Example 8 with the resultant compound of Example 5, gave the desired compound, m.p. 87°–88° C.

Anal. calcd. for $C_{14}H_{27}NO_4S$: C, 55.05; H, 8.91; N, 4.59. Found: C, 55.11; H, 9.31; N, 4.61.

EXAMPLE 10

(3S,4S)-4-Amino-3-hydroxy-6-methyl-1-phenethylmercaptoheptane

A solution of 4(S)-isobutyl-5(S)-[2-(phenethylmercapto)ethyl]-2-oxazolidinone (0.52 g, 1.69 mmol) and barium hydroxide octahydrate (1.06 g, 3.38 mmol) in dioxane (60 mL) and water (40 mL) was heated at reflux under $N_2$ for 21 hours. The solid barium carbonate was filtered and the filtrate was partially evaporated. The residue was diluted with water and the resulting solution was extracted with ether. The organic extract was washed with brine solution, dried over $MgSO_4$ and evaporated to a residue. Trituration with cold hexane gave 365 mg (77%) of product, m.p. 95°–96° C.

Anal. calcd. for $C_{16}H_{27}NOS$: C, 68.28; H, 9.67; N, 4.98. Found: C, 67.99; H, 9.66; N, 4.75.

EXAMPLE 11

(3S,4S)-4-Amino-3-hydroxy-1-isoamylmercapto-6methylheptane

Using the procedure of Example 10 with the resultant compound of Example 5, gave the desired compound, m.p. 64°–65° C.

Anal. calcd. for $C_{13}H_{29}NOS$: C, 63.10; H, 11.81; N, 5.66. Found: C, 63.34; H, 12.09; N, 5.50.

EXAMPLE 12

(3S,4S)-4-Amino-3-hydroxy-6-methyl-1-phenethylsulfonylheptane

Using the procedure of Example 10 with the resultant compound of Example 8, gave the desired compound, m.p. 153°–154° C.

Anal. calcd. for $C_{16}H_{27}NO_3S$ $1/4H_2O$: C, 61.31; H, 8.68; N, 4.47. Found: C, 60.66; H, 8.63; N, 4.19.

EXAMPLE 13

(3S,4S)-4-Amino-3-hydroxy-1-isoamylsulfonyl-6-methylheptane

Using the procedure of Example 10 with the resultant compound of Example 9, gave the desired compound, m.p. 125°–126° C.

Anal. calcd. for $C_{13}H_{29}NO_3s$: C, 55.88; H, 10.46; N, 5.01. Found: C, 55.75; H, 10.52; N, 4.65.

EXAMPLE 14

4(S)-Isobutyl-5(S)-(2-phenoxyethyl)-2-oxazolidinone

Using the procedure of example 4 but changing phenethyl mercaptan to phenol and THF to DMF gave the desired compound in 54% yield. Mass spectrum: $M^+ = 264$.

EXAMPLE 15

(3S,4S)-4-Amino-3-hydroxy-6-methyl-1-phenoxyheptane

Using the procedure of Example 10 with the resultant compound of Example 14, gave the desired compound as an oil in 82% yield. Mass spectrum: $M^+ = 238$.

EXAMPLE 16

Boc-Phe-Ala amide of (3S,4S)-4-amino-3-hydroxy-6-methyl-1-phenethylmercaptoheptane To a stirred −12° C. solution of Boc-Phe-Ala-OH (47.8 mg, 0.142 mmol) in anhydrous tetrahydrofuran (3 mL) were added N-methylmorpholine (15.6 microliters, 0.142 mmol) and isobutylchloroformate (18.4 microliters, 0.142 mmol) sequentially. After 3 minutes, a −12° C. solution of the resultant compound of Example 10 (0.142 mmol) in anhydrous tetrahydrofuran (2 mL) was added. Ten minutes later, the mixture was allowed to warm to room temperature for 2 hours, at which time the solvent was evaporated, and the resulting residue was partitioned between ethyl acetate (20 mL) and saturated $NaHCO_3$ (5 mL). The organic phase was washed sequentially with 0.01 M $H_3PO_4$ (3 mL) and brine (5 mL). Drying ($Na_2SO_4$) and evaporating provided 77 mg (90%) of the desired compound as a glass.

Anal. calcd. for $C_{33}H_{49}N_3O_5S$: C, 66.08; H, 8.23; N, 7.00. Found: C, 66.11; H, 8.35; N, 6.84.

EXAMPLE 17

Boc-Phe-Ala amide of (3S,4S)-4-amino-3-hydroxy-1-isoamylmercapto-6-methylheptane Using the procedure of Example 16 with the resultant compound of Example 11, gave the desired compound, m.p. 137°–138° C.

Anal. calcd. for $C_{30}H_{51}N_3O_5S$: C, 63.68; H, 9.09; N, 7.43. Found: C, 64.01; H, 8.93; N, 7.39.

EXAMPLE 18

Boc-Phe-Ala amide of
(3S,4S)-4-amino-3-hydroxy-6-methyl-1-phenethylsulfonylheptane Using the procedure of Example 8 with the resultant compound of Example 16, gave the desired compound, m.p. 186°–187° C.

Anal. calcd. for $C_{33}H_{49}N_3O_7S$: C, 62.74; H, 7.82; N, 6.65. Found: C, 62.67; H, 7.56; N, 6.61.

EXAMPLE 19

Boc-Phe-Ala amide of
(3S,4S)-4-amino-3-hydroxy-1-isoamylsulfonyl-6-methylheptane Using the procedure of Example 8 with the resultant compound of Example 17, gave the desired compound.

Anal. calcd. for $C_{30}H_{51}N_3O_7S$: C, 60.27; H, 8.60; N, 7.03. Found: C, 60.47; H, 8.29; N, 6.98.

EXAMPLE 20

Boc-Phe-Ala amide of
(3S,4S)-4-amino-3-hydroxy-1-isoamylsulfinyl-6-methylheptane Using the procedure of Example 8 but using only one molar equivalent of m-chloroperoxybenzoic acid and conducting the reaction at 0° C., the resultant compound from Example 17 was converted to the desired compound.

EXAMPLE 21

Boc-Phe-Ala amide of
(3S,4S)-4-amino-3-hydroxy-6-methyl-1-phenoxyheptane

Using the procedure of Example 16 with the resultant compound from Example 15, gave the desired compound.

EXAMPLE 22

Boc-Phe-His amide of
(3S,4S)-4-amino-3-hydroxy-11-isoamylsulfonyl-6-methylheptane To a stirred −23° C. solution of Boc-Phe-His-OH (153 mg, 0.38 mmol) in anhydrous dimethylformamide (5 mL) was added a solution of the compound from Example 13 (0.38 mmol) in dimethylformamide (3 mL). Hydroxybenzotriazole (HOBT, 77 mg, 0.57 mmol) and dicyclohexylcarbodiimide (DDC, 78 mg, 0.38 mmol) were then added sequentially. After 2.5 hours the mixture was warmed to 25° C., stirred 12 hours, filtered and evaporated to a residue which was partitioned between ethyl acetate (20 mL) and saturated NaHCO₃ (8 mL). The organic phase was then washed separately with saturated NaHCO₃ (8 mL) and brine (8 mL). Drying (Na₂SO₄) and evaporating provided a white solid which was chromatographed on SiO₂ (95/5, dichloromethane/methanol) to give 180 mg (75%) of the desired compound. Mass spectrum: (M+H)+ = 664.

EXAMPLE 23

Boc-Phe-His amide of
(3S,4S)-4-amino-3-hydroxy-6-methyl-1-phenethylsulfonylheptane Using the procedure of Example 22 with the resultant compound of Example 12, gave the desired compound.

Anal. calcd. for $C_{36}H_{51}N_5O_7S$: C, 61.96; H, 7.37; N, 10.03. Found: C, 61.38; H, 7.71; N, 9.07.

EXAMPLE 24

(5S,6S)-5-Acetoxy-6-t-butyloxycarbonylamino-8-methyl-1-nonene

Using the procedure of Example 1 but changing vinyl magnesium bromide to butenyl magnesium bromide, gave a 56% yield of (5S,6S)-6-t-butyloxycarbonylamino-5-hydroxy-8-methyl-1-nonene as an oil. A 25 g (0.092 mole) sample of this material was dissolved in methylene chloride (200 mL) containing 10 mL of pyridine. Acetic anhydride (11.74 g, 0.115 mole) was added by dropwise addition and the resulting mixture was stirred for 24 hours at room temperature. The mixture was washed successively with aqueous NaHCO₃, aqueous citric acid and brine solution. After drying over MgSO₄, the solvent was evaporated to a residue. Flash chromatography on silica gel gave an 82% yield of product as an oil.

Anal. calcd. for $C_{17}H_{31}NO_4$: C, 65.15; H, 9.97; N, 4.47. Found: C, 65.11; H, 9.66; N, 4.30.

EXAMPLE 25

4(S)-Isobutyl-5(S)-(4-butenyl)-2-oxazolidinone

A solution of the compound from Example 24 (33 g, 0.105 mole) dissolved in 150 mL of dimethylformamide and 50 mL of tetrahydrofuran was treated with 11 g (0.204 mole) of sodium methoxide in one portion. The reaction mixture was stirred overnight at room temperature and then poured into an acidified solution of aqueous NaCl with cooling. The resulting mixture was extracted with ether. The ethereal extract was washed three times with brine solution and dried over MgSO₄. Evaporation of the solvent gave 19.6 g (95%) of liquid product.

Anal. calcd. for $C_{11}H_{19}NO_2$: C, 66.97; H, 9.71; N, 7.10. Found: C, 67.25; H, 9.84; N, 6.91.

EXAMPLE 26

4(S)-Isobutyl-5(S)-(2-formylethyl)-2-oxazolidinone

To a stirred solution of the compound from Example 25 (5.0 g, 25.3 mmol) in dichloromethane (60 mL) was added m-chloroperbenzoic acid (MCPBA, 10.8 g of 80% MCPBA, 50 mmol). After 68 hours the reaction mixture was cooled to 0° C., and 0° C. 10% Na₂SO₃ was added with stirring. After 15 min, the solid was filtered off and extracted with dichloromethane. The combined organic phase was washed sequentially with 0° C. 10% Na₂SO₃, saturated NaHCO₄ and water. Drying (MgSO₄), filtering and evaporating provided crude epoxide which was chromatographed on silica gel eluting with 50/50 hexane-ethyl acetate to give a 73% yield of purified epoxide. A 10 g (0.047 mole) sample of the above epoxide was mixed with 200 mL of 6% perchloric acid and kept for 24 hours at room temperature. The solution was neutralized with solid sodium bicarbonate, saturated with sodium chloride and extracted with ethyl acetate. Evaporation of the solvent left 10 g of glycolic material as a viscous syrup. The above glycol (10 g, 0.043 mole) was dissolved in 150 mL of water and treated all at once with a solution of periodic acid (9.1 g, 0.04 mole) in 150 mL of water. After stirring at 25° C. for 5 hours, the mixture was extracted with methylene chloride. The dried methylene chloride solution was evaporated to give a quantitative yield of product.

EXAMPLE 27

4(S)-Isobutyl-5(S)-(6-methyl-3-oxoheptyl)-2-oxazolidinone

A 2 g (0.01 mole) portion of the compound from Example 26 was dissolved in THF (50 mL) and treated at 0°–5° C. with 37.5 mL of an 0.8 M solution of isopentyl magnesium bromide in THF. The reaction was stirred for 2 hours at room temperature and then poured into ice water which contained 6.5 mL of 6 N HCl. The mixture was extracted with methylene chloride. Evaporation of the dried methylene chloride solution gave a quantitative yield of the Grignard adduct. This material was dissolved in 300 mL of acetone and treated by dropwise addition with Jones solution until the orange color persisted. The chromium salts were filtered and the filtrate was evaporated. The residue was diluted with ether and the resulting solution was washed successively with aqueous $NaHCO_3$ and brine solution. After drying over $MgSO_4$, the solvent was evaporated to give 1.7 g (66%) of product as an oil. NMR (300 MHz, $CDCl_3$, ppm): 0.86–0.96 (m, 12H), 2.41 (M, 2H), 2.67 (m, 2H), 3.5 (m, 1H), 4.15 (m, 1H).

EXAMPLE 28

4(S)-Isobutyl-5(S)-(6-methyl-3-oxoheptyl)-2-oxazolidinone ethylene ketal

A mixture of the product from Example 27 (2.5 g, 9.3 mmol), ethylene glycol (7.5 mL) and p-toluenesulfonic acid (60 mg) in toluene (100 mL) was heated at reflux with a Dean-Stark trap for 8 hours. The cooled mixture was washed with aqueous $NaHCO_3$ and dried over $MgSO_4$. Evaporation of the solvent gave a residue which was flash chromatographed on silica gel eluting with 65/35 hexane-ethyl acetate to give 2.3 g (79%) of product. NMR (300 MHz, $CDCl_3$, ppm): 0.85–0.95 (4d, 12H), 3.5 (m, 1H), 3.95 (s, 4H), 4.15 (m, 1H).

EXAMPLE 29

(b 4S,5S)-4-Amino-2, 11-dimethyl-5-hydroxy-8-oxododecane ethylene ketal

Using the procedure of Example 10 with the resultant compound of Example 28, gave the desired compound in 73% yield, m.p. 26° C.

EXAMPLE 30

Boc-Phe-Ala amide of (4S,5S)-4-amino-2,11-dimethyl-5-hydroxy-8-oxododecane

Using the procedure of Example 16 with the resultant compound of Example 29, gave a 90% yield of the title compound as the corresponding ethylene ketal.

Anal. calcd. for $C_{33}H_{55}N_3O_7$: C, 65.43; H, 9.15; N, 6.94. Found: C, 65.28; H, 9.16; N, 6.67.

The desired deketalized product was obtained as follows. A solution of the ketal (400 mg) was stirred for 24 hours in 37 mL acetic acid/water/tetrahydrofuran (3/1/1). The solvents were evaporated under reduced pressure and the residue was triturated with hexane-ether (65:35) to give 280 mg (76%) of product, m.p. 137°–138° C.

Anal. calcd. for $C_{31}H_{51}N_3O_6$: C, 66.28; H, 9.15; N, 7.48. Found: C, 66.29; H, 9.23; N, 7.32.

EXAMPLE 31

(3S,4S)-3-Hydroxy-4-t-butyloxycarbonylamino-5-cyclohexylpentane nitrile

To a solution of lithium diisopropylamide (4.40 mmol) in dry tetrahydrofuran (4 mL) at −78° C. was added acetonitrile (0.25 mL, 4.4 mmol). To this enolate suspension was added 2(S)-t-butyloxycarbonylamino-3-cyclohexylpropanal (0.76 g, 2.98 mmol) in tetrahydrofuran (5 mL) pre-cooled to −78° C. After stirring for 15 minutes, the mixture was quenched with 2M HCl (5.0 mL), and extracted with ether which was dried over $MgSO_4$ and evaporated. Flash chromatography on silica gel with ethyl acetate/hexane mixtures afforded 0.360 g (41%) of the desired compound as an oil.

Anal. calcd. for $C_{16}H_{28}N_2O_3$ $0.4H_2O$: C, 63.30; H, b 9.56; N, 9.23. Found: C, 63.51; H, 9.66; N, 8.81.

EXAMPLE 32

(3S,4S)-3-Hydroxy-4-t-butyloxycarbonylamino-5-cyclohexylpentane nitrile (0.2300 g, 0.766 mmol) and Raney nickel (0.230 g) were hydrogenated at 3 atm in methanol (20 mL) and ammonia (15 mL). The mixture was filtered, evaporated, dissolved in ethyl acetate and extracted with 0.5M $H_3PO_4$. The aqueous phase was made basic with solid $K_2CO_3$ and extracted with 25% isopropanol in chloroform which was dried over $Na_2SO_4$ and evaporated to afford 0.1520 g (65%) of the desired product as an oil. Exact mass calculated for $C_{16}H_{32}N_2O_3$: 300.2411. Found: 300.2439.

EXAMPLE 33

(3S,4S)-1-(3-Methylbutylcarbonylamino)-3-hydroxy-4-t-butyloxycarbonylamino-5-cyclohexylpentane To (3S,4S)-1-amino-3-hydroxy-4-t-butyloxycarbonylamino-5-cyclohexylpentane (30.8 mg, 0.102 mmol) in dry methylene chloride (3 mL) at 0° C. was added 4-methylpentanoyl chloride (17.0 microliters, 0.123 mmol) and triethylamine (20.0 microliters, 0.143 mmol). The mixture was stirred at 0° C. for 1 hour, evaporated, taken up in methanol (3 mL) and treated with 1M NaOH (1 mL). After stirring for 1 hour, the mixture was diluted with ether, washed sequentially with 0.5M $H_3PO_4$, saturated $NaHCO_3$ solution, and brine, and then dried over $Na_2SO_4$ and evaporated to afford 41.0 mg (100%) of the desired product as an oil.

Anal. calcd. for $C_{16}H_{28}N_2O_3$ $0.25H_2O$: C, 65.55; H, 10.63; N, 6.95. Found: C, 65.52; H, 11.02; N, 6.77.

EXAMPLE 34

Boc-Phe-Ala Amide of (3S,4S)-1-(3-Methylbutylcarbonylamino)-3-hydroxy-4-amino-5-cyclohexylpentane (3S,4S)-1-(3-Methylbutylcarbonylamino)-3-hydroxy-4-t-butyloxycarbonylamino-5-cyclohexylpentane (26.8 mg, 0.0672 mmol) was stirred in 4M HCl/dioxane (1.5 mL) for 1 hours, and evaporated. The residue was dissolved in dry tetrahydrofuran (3 mL), treated with N-methylmorpholine (8.5 microliters, 0.077 mmol), and cooled to −12° C.

To Boc-Phe-Ala-OH (27.4 mg, 0.082 mmol) in dry tetrahydrofuran (3 mL) was added N-methylmorpholine (9.1 microliters, 0.083 mmol). The mixture was cooled to −12° C. and treated with isobutylchloroformate (10.6 microliters, 0.081 mmol). After stirring for 3 minutes the amine solution was added and the reaction was stirred for 15 minutes at −12° C. and 2 hours at room temperature. The mixture was diluted with ethyl acetate which was washed sequentially with 0.5M $H_3PO_4$, saturated $NaHCO_3$ solution, and brine, then dried over $Na_2SO_4$ and evaporated to 43.2 mg of a white solid. Trituration with ether afforded 25.4 mg (61%) of the desired product as a white solid mp. 176°–177° C.

Anal. calcd. for $C_{34}H_{56}N_4O_6$: C, 66.20; H, 9.15; N, 9.08. Found: C, 65.82; H, 9.14; N, 9.01.

EXAMPLE 35

Boc-Phe-His Amide of (3S,4S)-1-(3-Methylbutylcarbonylamino)-3-hydroxy-4-amino-5-cyclohexylpentane Using the procedure of Example 22 with the resultant compound of Example 33 which has been deprotected as described in Example 34, gave the desired compound, m.p. 168°–172° C.

EXAMPLE 36

Boc-His Amide of (3S,4S)-1-(3-Methylbutylcarbonylamino)-3-hydroxy-4-amino-5-cyclohexylpentane Using the procedure of Example 22 with the resultant compound of Example 33 and Boc-His-OH rather than Boc-Phe-His-OH, gave the desired compound.

EXAMPLE 37

Dba-His Amide of (3S,4S)-1-(3-Methylbutylcarbonylamino)-3-hydroxy-4-amino-5-cyclohexylpentane Using the procedure of Example 22 employing the resultant compound from Example 36 which had been deprotected as described in Example 34 and 2,2-dibenzylacetic acid (Dba) rather than Boc-Phe-His-OH, gave the desired compound.

EXAMPLE 38

Tba-Phe-His Amide of (3S,4S)-1-(3-Methylbutylcarbonylamino)-3-hydroxy-4-amino-5-cyclohexylpentane Using the procedure of Example 37 employing the resultant compound from Example 36 and t-butylacetyl-Phe-OH (Tba-Phe) rather than Boc-Phe-His-OH, gave the desired compound.

EXAMPLE 39

3-t-Butyloxycarbonylamino-5-methylhex-1-ene

To a stirred suspension of methyltriphenyl phosphonium bromide (10.97 g, 30.70 mmol) in anhydrous tetrahydrofuran (200 mL) at −78° C. (dry ice/acetone bath) under an argon atmosphere, was added n-butyl lithium, (19.8 mL of a 1.55 M hexane solution) dropwise over the course of 5 minutes. After 10 minutes, the −78° C. bath was replaced with a 0° C. bath for one-half hour, at which time the resulting orange solution was cooled again to −78° C. The solution was then added dropwise by cannula to a stirred −78° C. solution of Boc-leucinal (6.00 g, 27.91 mmol) in anhydrous tetrahydrofuran (30 mL) over the course of one-half hour. The mixture was then allowed to warm to room temperature during a 3 hour period after which water (150 mL) was added. Extraction with hexane (4×100 mL) provided a combined organic phase which was washed with brine (100 mL), dried ($Na_2SO_4$), and concentrated to give crude 3-t-butyloxycarbonylamino-5-methylhex-1-ene (6.5 g). Chromatography with ether/hexane (1/9) provided pure 3-t-butyloxycarbonylamino-5-methylhex-1-ene (3.71 g, 60%). Mass spectrum: EI, $M^+$-57=156; CI, $(M+H)^{30}$=214.

EXAMPLE 40

3-t-Butyloxycarbonylamino-5-methyl-1,2-oxohexane

To a stirred solution of 3-t-butyloxycarbonylamino-5-methylhex-1-ene (0.43 g, 2.0 mmol) in dichloromethane (20 mL) was added m-chloroperbenzoic acid (MCPBA, 1.51 g of 80% MCPBA, 7.0 mmol). After 68 hours the reaction mixture was cooled to 0° C., and 0° C. 10% $Na_2SO_3$ (5 mL) was added with stirring. After 15 minutes, the solid was filtered off and extracted with dichloromethane. The combined organic phase was washed sequentially with 0° C. 10% $Na_2SO_3$ (6 mL), saturated $NaHCO_3$ (2×6 mL), and water (5 mL). Drying ($MgSO_4$), filtering and evaporating provided crude 3-t-butyloxycarbonylamino-5-methyl-1, 2-oxohexane (0.42 g) which was chromatographed on 50 g of $SiO_2$ (hexane/ether, 3/1) to give pure 3-t-butyloxycarbonylamino-5-methyl-1,2-oxohexane (0.27 g, 59%). Mass spectrum: $M^+$=229.

EXAMPLE 41

4-t-Butyloxycarbonylamino-3-hydroxy-6-methyl1-(4-methylvaleryl)amino-1-phenylheptane To a stirred 0° C. solution of N-benzylvaleramide (600 mg, 2.92 mmol) in dry THF (20 mL) was added butyl lithium (4.17 mL of a 1.32 M solution in hexane). The solution was cooled to −78° C. and a solution of the resultant product of Example 40 (300 mg, 1.31 mmol) in THF (6 mL) was added dropwise. Saturated $NH_4Cl$ (20 mL) and water (20 mL) were added 1.5 hours later. Ether (75 mL) and 1 M $H_3PO_4$ (5 mL) were then added. The layers were separated, and the organic phase was washed with saturated $NaHCO_3$ (15 mL) and brine (15 mL). Drying and evaporating provided an oil which was chromatographed on 100 g $SiO_2$ with $CH_2Cl_2/CH_3OH$ mixtures to give 378 mg, (67%) of the desired material. Mass spectrum: $M^+$=434.

EXAMPLE 42

Boc-Phe-Ala amide of 4-amino-3-hydroxy-6-methyl-1-(4-methylvaleryl)amino-1-phenylheptane Following the deprotection procedure of Example 34 and using the resultant compound of Example 41 gave the corresponding amine hydrochloride which was coupled to Boc-Phe-Ala according to the procedure of Example 34. The desired compound was obtained in 98% yield. Mass spectrum: $(M+H)^+$=653.

Anal. calcd.: C, 68.1; H, 8.7; N, 8.6. Found: C, 68.1; H, 9.0; 8.3.

EXAMPLE 43

4-t-Butyloxycarbonylamino-1-cyclohexyl-3-hydroxy-6-methyl-1-(4-methylvaleryl)aminoheptane The resultant compound of Example 41 (70.0 mg, 0.161 mmol) in glacial acetic acid (15 mL) was hydrogenated over Pt black (70 mg) for 22 hours. The mixture was filtered, diluted with $H_2O$ (50 mL) and brine (50 mL), and extracted with ether (50 mL). The organic phase was washed with water (2×50 mL), saturated K₂CO₃ (25 mL), and brine (10 mL). Drying (MgSO₄) and evaporating gave 54 mg of the desired material. Mass spectrum: (M+H)+ =441.

Anal. calcd.: C, 68.1; H, 11.0; N, 6.4. Found: C, 68.3; H, 11.5; N, 6.3.

EXAMPLE 44

Boc-Phe-Ala amide of 4-amino-1-cyclohexyl-3-hydroxy-6-methyl-1-(4-methylvaleryl)aminoheptane Following the deprotection procedure of Example 34 and using the resultant compound of Example 43 gave the corresponding amine hydrochloride which was coupled to Boc-Phe-Ala according to the procedure of Example 34, the desired compound was obtained in 89% yield. Mass spectrum: M+ =658.

EXAMPLE 45

5-t-Butyloxycarbonylamino-4-hydroxy-7-methyl-2-phenyloctanoic acid isoamyl amide Using the procedure of Example 41, but replacing 4-methylvaleric benzamide with N-isoamyl phenylacetamide gave the desired compound in 15% yield after chromatography.

EXAMPLE 46

Boc-Phe-Ala amide of 5-amino-4-hydroxy-77-methyl-2-phenyloctanoic acid isoamyl amide Following the deprotection procedure of Example 34 and using the resultant compound of Example 45 gave the corresponding amine hydrochloride which was coupled to Boc-Phe-Ala according to the procedure of Example 34. The desired compound was obtained in 76% yield. Mass spectrum: M+ =652.

Anal. calcd. for $C_{37}H_{56}N_4O_6$: C, 68.1; H, 8.7; N, 8.6. Found: C, 67.8; H, 8.7; N, 8.1.

EXAMPLE 47

5-t-Butyloxycarbonylamino-2-cyclohexyl-4-hydroxy-7-methyloctanoic acid isoamyl amide The resultant compound of Example 45 was hydrogenated according to the procedure of Example 43 to give the desired compound in 68% yield.

EXAMPLE 48

Boc-Phe-Ala amide of 5-amino-2-cyclohexyl-4-hydroxy-7-methyloctanoic acid isoamyl amide Following the deprotection of Example 34 and using the resultant compound of Example 47 gave the corresponding amine hydrochloride which was coupled to Boc-Phe-Ala according to the procedure of Example 34. The desired compound was obtained in 82% yield.

EXAMPLE 49

(3S,4S)-1-(2-Propylsulfonylamino)-3-hydroxy-4-t-butyloxycarbonylamino-5-cyclohexylpentane Using the procedure of Example 33 employing the resultant compound from example 32 and isopropylsulfonyl chloride instead of 4-methylpentanoyl chloride afforded the desired compound.

EXAMPLE 50

Boc-Phe-His Amide of (3S,4S)-1-(2-propylsulfonylamino)-3-hydroxy-4-amino-5-cyclohexylpentane Using the procedure of Example 22 employing the resultant compound from Example 49 which had been deprotected as described in Example 34 gave the desired compound, m.p. 174°–177° C.

EXAMPLE 51

Boc-3-methyl-His Amide of (3S,4S)-1-(3-Methylbutylcarbonylamino)-3-hydroxy-4-amino-5-cyclohexylpentane Using the procedure of Example 22 with the resultant compound of Example 33 which had been deprotected as described in example 34 and using Boc-3-methyl-His-OH rather than Boc-Phe-His-OH, gave the desired compound.

Anal. calcd. For $C_{29}H_{51}N_5O_5$ 0.5H₂O: C, 62.34; H, 9.38; N, 12.53. Found: C, 62.43; H, 9.38; N, 12.25.

EXAMPLE 52

Boc-Phe-3-methyl-His Amide of (3S,4S)-1-(3-Methylbutylcarbonylamino)-3-hydroxy-4-amino-5-cyclohexylpentane Using the procedure of Example 22 with the resultant compound of Example 51 which had been deprotected as described in Example 34 and Boc-Phe-OH rather than Boc-Phe-His-OH gave the desired compound.

Anal.calcd. For $C_{38}H_{60}N_6O_6$ 0.75H₂O: C, 64.24; H, 8.72; N, 11.83. Found: C, 64.46; H, 8.80; N, 11.44.

EXAMPLE 53

Boc-Phe-Phe Amide of (3S,4S)-1-(3-Methylbutylcarbonylamino)-3-hydroxy-4-amino-5-cyclohexylpentane Using the procedure of Example 34 with the resultant compound of Example 33 and Boc-Phe-Phe-OH rather than Boc-Phe-Ala-OH gave the desired compound.

Anal. calcd. For $C_{40}H_{60}N_4O_6$ H₂O: C, 67.58; H, 8.79; N, 7.88. Found: C, 67.57; H, 8.67; N, 7.66.

EXAMPLE 54

Boc-Phe-dl-3-pyrazolylalanine Methyl Ester

To dl-3-pyrazolylalanine methyl ester dihydrochloride (dl connotes 50/50 mixture of dextrorotatory/levorotatory) (2.05 g, 8.5 mmol) in dimethylformamide (10 mL) at −10° C. was added Boc-Phe N-hydroxysuccinimide ester (2.50 g, 6.90 mmol) and N-methylmorpholine (2.8 mL, 25 mmol). The mixture was stirred at −10° C. for 1 hour and then at 25° C. for 12 hours. The mixture was partitioned between ethyl acetate and saturated NaHCO₃ solution, and extracted with ethyl acetate which was washed with water, dried over Na₂SO₄ and evaporated to afford 2.75 g (95%) of the desired product.

Anal. calcd. For $C_{21}H_{28}N_4O_5$ 0.25H₂O: C, 59.92; H, 6.82; N, 13.31. Found: C, 59.82; H, 6.75: N, 13.13.

EXAMPLE 55

Boc-Phe-dl-4-thiazolylalanine Methyl Ester

Using the procedure of Example 54 and employing dl-4-thiazolylalanine methyl ester dihydrochloride rather than dl-3-pyrazolylalanine methyl ester dihydrochloride afforded the desired compound.

Anal. calcd. For $C_{21}H_{27}N_3O_5S$ 0.25 $H_2O$: C, 57.58; H, 6.33; N, 9.59. Found: C, 57.63; H, 6.48; N, 9.25.

EXAMPLE 56

Boc-Phe-dl-3-pyrazolylalanine

Boc-Phe-dl-3-pyrazolylalanine methyl ester (0.210 g, 0.505 mmol) in dioxane (1.5 mL) and water (1.0 mL) was treated with lithium hydroxide monohydrate (0.0272 g, 0.648 mmol), stirred at 25° C. for 30 minutes and quenched with 0.32 mL 2 M HCl. The mixture was poured into chloroform, washed with water, dried over $Na_2SO_4$ and evaporated to afford 0.184 g (91%) of the desired compound.

Anal. calcd. For $C_{20}H_{26}N_4O_5$ 0.25$H_2O$: C, 59.03; H, 6.56; N, 13.77. Found: C, 58.66; H, 6.70; N, 13.65.

EXAMPLE 57

Boc-Phe-dl-4-thiazolylalanine

Using the procedure of Example 56 with the resultant compound from example 55 rather than Boc-Phe-dl-3-pyrazolylalanine methyl ester afforded the desired compound.

Anal. calcd. for $C_{20}H_{25}N_3O_5S$ 0.5$H_2O$: C, 56.06; H, 6.12; N, 9.81. Found: C, 56.27; H, 6.28; N, 9.75.

EXAMPLE 58

Boc-Phe-dl-3-pyrazolylalanine Amide of (3S,4S)-1-(3-Methylbutylcarbonylamino)-3-hydroxy-4-amino-5-cyclohexylpentane Using the procedure of Example 22 with the resultant compound from Example 33 which had been deprotected as described in Example 34 and using the resultant compound from example 56 rather than Boc-Phe-His-OH afforded the desired compound.

Anal. calcd. for $C_{37}H_{58}N_6O_6$ 0.75$H_2O$: C, 63.81; H, 8.61; N, 12.07. Found: C, 63.95; H, 8.70; N, 11.79.

EXAMPLE 59

Boc-Phe-dl-4-thiazolylalanine Amide of (3S,4S)-1-(3-Methylbutylcarbonylamino)-3-hydroxy-4-amino-5-cyclohexylpentane Using the procedure of Example 22 with the resultant compound from Example 33 which had been deprotected as described in Example 34 and using the resultant compound from example 57 rather than Boc-Phe-His-OH afforded the desired compound.

Anal. calcd. for $C_{37}H_{57}N_5O_6S$ $H_2O$: C, 61.90; H, 8.28; N, 9.75. Found: C, 62.01; H, 8.42; N, 9.79.

EXAMPLE 60

Boc-dl-4-pyrimidinylalanine

To dl-4-pyrimidinylalanine (0.35 g, 2.31 mmol) in a solution of sodium hydroxide (0.105 g, 2.62 mmol) in water (2.5 mL) and tert-butanol (1.7 mL) was added di-tert-butyldicarbonate (0.520 g, 2.39 mmol) in tetrahydrofuran (0.5 mL). The mixture was stirred for 16 hours, poured into saturated $NaHCO_3$ solution and washed with ether. The aqueous phase was acidified with 2 M HCl to pH 5-6 and the resulting solid was filtered and dried affording 0.417 g (71%) of the desired compound.

Anal. calcd. for $C_{12}H_{17}N_3O_4$: C, 53.92; H, 6.41; N, 15.72. Found: C, 54.20; H, 6.41; N, 15.63.

EXAMPLE 61

Boc-dl-4-pyrimidinylalanine Amide of (3S,4S)-1-(3-Methylbutylcarbonylamino)-3-hydroxy-4-amino-5-cyclohexylpentane Using the procedure of Example 22 with the resultant compound of Example 33 which had been deprotected as described in Example 34 and using the resultant compound from example 60 rather than Boc-Phe-HisOH afforded the desired compound.

Anal. calcd. for $C_{29}N_{49}N_5O_5$ 0.75$H_2O$: C, 62.09; H, 9.07; N, 12.48. Found: C, 62.52; H, 8.87; N, 12.08.

EXAMPLE 62

Boc-Phe-dl-4-pyrimidinylalanine Amide of (3S,4S)-1-(3-Methylbutylcarbonylamino)-3-hydroxy-4-amino-5-cyclohexylpentane Using the procedure of Example 22 with the resultant compound of Example 61 which had been deprotected as described in Example 34 and using Boc-Phe-OH rather than Boc-Phe-His-OH afforded the desired compound.

Anal. calcd. for $C_{38}H_{58}N_6O_6$ 0.5$H_2O$: C, 64.84; H, 8.45; N, 11.94. Found: C, 64.86; H, 8.56; N, 11.91.

EXAMPLE 63

Ethyl (2-Propylmercapto)acetate

To sodium (4.2 g, 0.18 mol) in ethanol (100 mL) was added 2mercaptopropane (20 mL), 0.21 mol) followed by ethyl bromoacetate (10 mL, 0.090 mol). The mixture was stirred for 12 hours, concentrated, partitioned between ether and water and washed with water. The organic phase was dried over $MgSO_4$, evaporated and distilled to afford the desired product. B.P. 58°-62° C. (1 mm).

EXAMPLE 64

(2-Propylmercapto) Acetic Acid

The resultant compound from Example 53 (0.61 g, 3.7 mmol) in ethanol (8 mL) was stirred with 4 mL 2 M NaOH for 90 minutes. The mixture was poured into 2 M HCl and extracted with chloroform which was dried over $Na_2SO_4$ and evaporated to afford 0.49 g (97%) of the desired compound.

EXAMPLE 65

(3S,4S)-1-(2-propylmercaptoacetylamino)-3-hydroxy-4-tertbutyloxycarbonylamino-5-cyclohexylpentane To (2-propylmercapto)acetic acid (44.3 mg, 0.33 mmol) in the THF (3 mL) at 0°(b) was added N-methylmorpholine (37 microliters, 0.34 mmol) followed by isobutylchloroformate (43 microliters, 0.33 mmol). The mixture was stirred at 0° C. for 15 minutes and (3S,4S)-1-amino-3-hydroxy-4-t-butyloxycarbonylamino-5-cyclohexylpentane (51.0 mg, 0.17 mmol) was added followed by stirring at 0° C. for 15 minutes and at 25° C. for 2 hours. The mixture was poured into ethyl acetate, washed with 0.5 M $H_3PO_4$, 2 M $Na_2SO_4$ and evaporated to afford 36 mg (50%) of the desired compound. Mass spectrum: $(M+1)^+=417$.

EXAMPLE 66

(3S,4S)-1-(2-Propylsulfonylacetylamino)-3-hydroxy-4-tert-butyloxycarbonylamino-5-cyclohexylpentane Using the procedure of Example 8 with the resultant compound from Example 65 afforded the desired compound.

Anal. calcd. for $C_{21}H_{40}N_2O_6S \cdot H_2O$: C, 54.05; H, 9.07; N, 6.00. Found: C, 54.33; H, 8.72; N, 5.84.

EXAMPLE 67

Boc-Phe-His Amide of (3S,4S)-1-(2-Propylmercaptoacetylamino)-3-hydroxy-4-amino-5-cyclohexylpentane Using the procedure of Example 22 with the resultant compound from Example 65 which had been deprotected as described in Example 34 afforded the desired compound, m.p. 154°–158° C.

EXAMPLE 68

Boc-Phe-His Amide of (3S,4S)-1-(2-Propylsulfonylacetylamino)-3-hydroxy-4-amino-5-cyclohexylpentane Using the procedure of Example 22 with the resultant compound from Example 66 which had been deprotected as described in Example 34 afforded the desired compound, m.p. 147°–150° C.

Anal. calcd. for $C_{36}H_{56}N_6O_8S \cdot 1.5H_2O$: C, 56.90; H, 7.82; N, 11.06. Found: C, 56.91; H, 7.82; N, 10.77.

EXAMPLE 69

Ethyl (3R,4S)-3-hydroxy-4-t-butyloxycarbonylamino-2,2-difluoro-5-cyclohexylpentanoate Boc-cyclohexylalanal (6.60 g, 25.8 mmol) in dry THF (100 mL) was treated with ethyl bromodifluoroacetate (10.5 g, 51.7 mmol) and zinc dust (4.25 g, 65.0 mmol). The mixture was subjected to ultrasonic mixing (15°–25° C.) for 2 hours, then poured into saturated aqueous NaHCO solution which was extracted with ethyl acetate. The organic phases were dried over $Na_2SO_4$, evaporated, and the residue was chromatographed on silica gel with ethyl acetate/hexane mixtures to afford 3.27 g (33%) of the desired compound and 1.45 g (15%) of the 3S isomer. 3R isomer: m.p. 106°–109° C.; 3S isomer: m.p. 71°–73° C.

EXAMPLE 70

(3R,4S)-1,3-dihydroxy-2,2-difluoro-4-t-butyloxycarbonylamino-5-cyclo-hexylpentane To the resultant compound from Example 69 (525.0 mg, 1.38 mmol) in methanol (6 mL) was added $NaBH_4$ (106 mg, 2.8 mmol). The mixture was stirred for 1 hour, poured into saturated aqueous $NaHCO_3$ solution, and extracted with ethyl acetate which was dried over $Na_2SO_4$ and evaporated to afford 467 mg (100%) of the desired product. Mass spectrum: CI, $(M+H)^+ = 338$.

EXAMPLE 71

(5R,4S)-4-Cyclohexylmethyl-5-(2-hydroxy-1,1-difluoroethyl)-2-oxazolidinone

The resultant compound from Example 70 (596 mg, 1.77 mmol) in dry DMF (15 mL) was added to NaH (260 mg, 6.5 mmol, 60% in oil, hexane washed) in DMF (5 mL) at 0° C. The mixture was stirred at room temperature for 16 hours and the solvent was removed under reduced pressure. The residue was partitioned between ethyl acetate and saturated aqueous $NaHCO_3$ solution and the organic phase was dried over $Na_2SO_4$ and evaporated to afford 472 mg (100%) of product as an oil.

Anal. calcd. for $C_{12}H_{19}F_2NO_3 \cdot 0.25H_2O$: C, 53.82; H, 7.34; N, 5.23. Found: C, 54.01; H, 7.05; N, 5.32.

EXAMPLE 72

(5R,4s)-4-cyclohexylmethyl-5-(2-mesyloxy-1,1-difluoroethyl)-2-oxizolidinone

To the resultant compound from Example 71 (460 mg, 1.75 mmol) in $CH_2Cl_2$ (5 mL) at 0° C. was added triethylamine (0.36 mL, 2.6 mmol) and methanesulfonyl chloride (135 microliters, 1.74 mmol). After stirring at 0° C. for 20 minutes, the mixture was diluted with ethyl acetate, washed sequentially with 0.5M $H_3PO_4$, saturated aqueous $NaHCO_3$ solution, and brine, then dried over $Na_2SO_4$ and evaporated to afford 558 mg (94%) product as an oil. Mass spectrum: FAB, $(M+H)^+ = 342$.

EXAMPLE 73

(5R,4S)-4-Cyclohexylmethyl-5-(2-azido-1,1-difluoroethyl)-2-oxizolidinone

To the resultant compound from Example 72 (179.9 mg, 0.527 mmol) in DMF (3 mL) was added $NaN_3$ (111.0 mg, 1.71 mmol) and the mixture was heated 100°–110° C. for 16 hours. The mixture was poured into ethyl acetate which was washed with water and brine, dried over $Na_2SO_4$ and evaporated. Chromatography of the residue and silica gel with ethyl acetate/hexane mixtures afforded 116.9 mg (77%) product as an oil. Mass spectrum: EI, $(M+H)^+ = 289$.

EXAMPLE 74

(5R,4S)-4-Cyclohexylmethyl-5-(2-isopropylmercapto-1,1-difluoroethyl)-2-oxizolidinone To NaH (85.0 mg, 2.22 mmol, 60% in oil, hexane washed) in DMF (4 mL) at 0° C. was added isopropylmercaptan (0.40 mL, 4.3 mmol). After 15 minutes the resultant compound from Example 72 (373.4 mg, 1.09 mmol) in DMF (4 mL) was added and the mixture was heated 50°–60° C. for 16 hours. The mixture was poured into ethyl acetate which was washed with water and brine, dried over $Na_2SO_4$ and evaporated. Chromatography of the residue on silica gel with ethyl acetate/hexane mixtures afforded 258.0 mg (73%) product as a solid, m.p. 75°–76° C.

Anal. calcd. for $C_{15}H_{25}F_2NO_2S$: C, 56.05; H, 7.84, N, 4.36. Found: C, 56.09, H, 8.02, N, 4.14.

EXAMPLE 75

(5R,4S)-4-Cyclohexylmethyl-5-(2-isopropyloxy-1,1-difluoroethyl)-2-oxizolidinone

Using the procedure of Example 74 and isopropanol instead of isopropyl mercaptan afforded the desired product.

EXAMPLE 76

(3R,4S)-3-Hydroxy-4-amino-2,2-difluoro-1-azido-5-cyclohexylpentane

To the resultant compound from Example 73 (113.9 mg, 0.395 mmol) in dioxane (4.5 mL) and water (3 mL) was added $Ba(OH)_2 \cdot 8H_2O$ (0.25 g, 0.79 mmol) and the mixture was heated at reflux for 13 hours. The mixture was filtered, and the filtrate was concentrated, partitioned between water and ether, and extracted with ether. The organic extract was dried over Na$_2$SO$_4$ and evaporated to afford 108 mg (100%) product as an oil. Mass spectrum: FAB, (M+H)$^+$ = 263.

EXAMPLE 77

(3R,4S)-3-Hydroxy-4-amino-2,2-difluoro-1-isopropyloxy-5-cyclohexylpentane

Using the procedure of Example 76 with the resultant compound from Example 75 afforded the desired compound.

EXAMPLE 78

Boc-Phe-Leu amide of (3R,4S)-3-hydroxy-4-amino-2,2-difluoro-1-azido-5-cyclohexylpentane To Boc-Phe-Leu-OH (169.8 mg, 0.449 mmol) in THF (2 mL) at −10° c. was added N-methylmorpholine (48 microliters, 0.44 mmol) followed by isobutyl chloroformate (57 microliters, 0.44 mmol). After 3 minutes, the resultant compound from Example 8 (105.0 mg, 0.40 mmol) in THF (4 mL) was added and the reaction was stirred at −10° C. 15 minutes then at room temperature for 2 hours. The mixture was diluted with ethyl acetate, washed sequentially with 0.5 M H$_3$PO$_4$, saturated aqueous NaHCO$_3$ solution, and brine, then dried over Na$_2$SO$_4$ and evaporated. Chromatography of the residue on silica gel with ethyl acetate/hexane mixtures afforded 184.0 mg (74%) product as a glass. NMR (300 MHz, CDCl$_3$, ppm):0.9 (d, 6H), 1.4 (5, 9H), 3.15–3.00 (m, 2H), 3.80–3.60 (m, 3H), 4.05–3.95 (m, 1H), 4.4–4.2 (m, 2H), 4.85 (d, 1H), 5.10 (d, 1H), 6.15 (d, 1H).

EXAMPLE 79 t-Butylacetyl-Phe-Leu amide of (3R,4S)-3-hydroxy-4-amino-2,2-difluoro-1-azido-5-cyclohexylpentane Using the procedure of Example 78 and using t-butylacetyl-Phe-Leu-Oh rather than Boc-Phe-Leu-OH afforded the desired product.

EXAMPLE 80

Boc-Phe-Phe amide of (3R,4s)-3-hydroxy-4-amino-2,2-difluoro-1-azido-5-cyclohexylpentane Using the procedure of Example 78 and using Boc-Phe-Phe-OH rather than Boc-Phe-Leu-OH afforded the desired product.

EXAMPLE 81 Boc-Phe-His amide of (3R,4S)-3-hydroxy-4-amino-2,2-difluoro-1-azido-5-cyclohexylpentane To Boc-Phe-HisOH (160.0 mg, 0.398 mmol) and 1-hydroxybenzotriazole (162.0 mg, 1.20 mmol) in DMF (2 mL) at −23° C. was added 1-(3-dimethylaminopropyl)-3-ethylcarbodiimide hydrochloride (76.0 mg, 0.396 mmol). After 1 hour the resultant compound from example 8 (95.0 mg, 0.362 mmol) and N-methylmorpholine (43 microliters, 0.39 mmol) in DMF (3 mL) were added. The mixture was stirred at −23° C. for 2 hours and at room temperature for 12 hours, then poured into saturated aqueous NaHCO$_3$ solution and extracted with ethyl acetate. The organic phases were washed with water then brine, dried over Na$_2$SO$_4$, and evaporated. Chromatography of the residue on silica gel with methanol/chloroform mixtures provided 117.0 mg (50%) of the desired product.

EXAMPLE 82

Boc-Phe-Leu amide of (3R,4S)-3-hydroxy-4-amino-2,2-difluoro-1-isopropyloxy-5-cyclohexylpentane Using the procedure of Example 78 with the resultant compound from example 77 afforded the desired product.

EXAMPLE 83

Boc-Phe-Leu amide of (3R,4S)-3-hydroxy-4-amino-2,2-difluoro-1-isopropylmercapto-5-cyclohexylpentane (A); Boc-Phe-Leu amide of (3R,4S,EZ)-3-hydroxy-4-amino-2-fluoro-1-isopropylmercapto-5-cyclohexyl-1-pentene (B)

Using the procedure of Example 78 and the resultant compound from example 74 which had been hydrolyzed to the free amine according to the procedure in Example 76 afforded the desired products.

Product A: Analysis calculated for C$_{34}$H$_{55}$F$_2$N$_3$O$_5$S: C, 62.26; H, 8.45; N, 6.41. Found: C, 62.32; H, 8.78; N, 6.19.

Product B: Mass spectrum: CI, (M+H)$^+$ = 636.

EXAMPLE 84

Boc-Phe-Leu amide (4-amino) of (3R,4S)-3-hydroxy-1,4-diamino-2,2-difluoro-5-cyclohexylpentane The resultant compound from example 78 (72.0 mg) and 10% palladium on carbon (42 mg) in methanol (3 mL) and acetic acid (1 mL) were stirred under a hydrogen atmosphere for 8 hours. The mixture was filtered, concentrated, and partitioned between ethyl acetate and 1 M aqueous Na$_2$CO$_3$ solution. The organic extracts were dried over Na$_2$SO$_4$ and evaporated to afford 63.2 mg (92%) of the desired product as a solid. Mass spectrum: EI, M$^+$ = 596.

EXAMPLE 85

Boc-Phe-Leu amide of (3R,4S)-3-hydroxy-4-amino-2,2-difluoro-1-isopentylcarbonylamino-5-cyclohexylpentane To the resultant compound from Example 84 (58.6 mg, 0.0982 mmol) in CH$_2$Cl$_2$(2 mL) at 0° C. was added N-methylmorpholine (16 microliters, 1.5 mmol) and isocaproyl chloride (15 microliters, 0.11 mmol). After stirring at room temperature for 1 hour the mixture was diluted with ethyl acetate, washed sequentially with 0.5 M H$_3$PO$_4$, saturated aqueous NaHCO$_3$ solution and brine, dried over Na$_2$SO$_4$ and evaporated. Chromatography of the residue on silica gel with ethyl acetate/hexane mixtures afforded 39.6 mg (58%) product as a solid.

Anal. calcd. for C$_{37}$H$_{60}$F$_2$N$_4$O$_6$: C, 63.95; H, 8.70; N, 8.06. Found: C, 64.07; H, 9.07; N, 7.73.

EXAMPLE 86

Boc-Phe-Leu amide of (3R,4S)-3-hydroxy-4-amino-2,2-difluoro-1-isopropylsulfonyl-5-cyclohexylpentane To the resultant compound from Example 83 (A) (50.0 mg, 0.0762 mmol) in CH$_2$Cl$_2$ (2 mL) was added m-chloroperbenzoic acid (42.0 mg, 0.20 mmol, 80% pure). After 1 hour the mixture was diluted with ethyl acetate, washed sequentially with cold 10% aqueous Na₂SO₃ solution, saturated aqueous NaHC₃ solution and brine, then dried over Na₂SO₄ and evaporated. Chromatography on silica gel with ethyl acetate/hexane mixtures provided 42.4 mg (81%) product as a solid.

Anal. calcd. for $C_{34}H_{55}F_2N_3O_7S$: C, 59.37; H, 8.06; N, 6.11. Found: C, 59.05; H, 8.33; N, 5.76.

EXAMPLE 87

Boc-Phe-Leu amide of (3R,4S,EZ)-3-hydroxy-4-amino-2-fluoro-1-isopropylsulfonyl-5-cyclohexyl-1-pentene Using the procedure of Example 86 with the resultant compound from Example 83 (B) provided the desired product. NMR (300 MHz, CDCl₃, ppm):0.95–0.85 (m, 6H), 1.40–1.30 (m, 6H), 1.40 (S, 9H), 6.08, 5.97 (d, J=33, 20 Hz, Total, 1H). Mass spectrum: EI, (M+H)⁺=668.

EXAMPLE 88

Boc-Phe-Leu amide of (4S)-3-oxo-4-amino-2,2-difluoro-1-azido-5-cyclohexylpentane To oxalyl chloride (19 microliters, 0.22 mmol) in CH₂Cl₂ (1 mL) at −60° C. was added dimethylsulfoxide (24 microliters, 0.34 mmol) in Ch₂Cl₂ (1 mL). After 15 minutes the resultant compound from Example 78 (44.0 mg, 0.0707 mmol) in Ch₂Cl₂ (3 mL) was added. The reaction was stirred for 20 minutes and triethylamine (75 microliters, 0.54 mmol) was added. The mixture was stirred for 20 minutes, poured quickly into cold 20% saturated aqueous NaHSO₄ solution and diluted with ethyl acetate (4 mL) and hexane (12 mL). The organic phase was washed with water then brine, dried over Na₂SO₄ and evaporated. Chromatography of the residue on silica gel with ethyl acetate/hexane mixtures provided 37.3 mg (85%) product as a solid. Mass spectrum: EI, M⁺=620.

EXAMPLE 89 t-Butylacetyl-Phe-Leu amide of (4S)-3-oxo-4-amino-2,2-defluoro-1-azido-5-cyclohexylpentane Using the procedure of Example 88 with the resultant compound from Example 79 provided the desired product.

EXAMPLE 90

Boc-Phe-Phe amide of (4S)-3-oxo-4-amino-2,2-difluoro-1-azido-5-cyclohexylpentane Using the procedure of Example 88 with the resultant compound from example 80 provided the desired product.

EXAMPLE 91

Boc-Phe-His amide of (4S)-3-oxo-4-amino-2,2-difluoro-1-azido-5-cyclohexylpentane Using the procedure of Example 88 with the resultant compound from Example 81 provided the desired product.

EXAMPLE 92

Boc-Phe-Leu amide of (4S)-3-oxo-4-amino-2,2-difluoro-1-isopropyloxy-5-cyclohexylpentane Using the procedure of Example 88 with the resultant compound from Example 82 provided the desired product.

EXAMPLE 93

Boc-Phe-Leu amide of (4S)-3-oxo-4-amino-2,2-difluoro-1-isopropylmercapto-5-cyclohexylpentane Using the procedure of Example 88 with the resultant compound from example 83 (A) provided the desired product as a solid.

Analysis calculated for $C_{34}H_{53}F_2N_3O_5S$ 0.5H₂O: C, 61.61; H, 8.21; N, 6.34. Found: C, 61.68; H, 8.25; N, 6.22.

EXAMPLE 94 Boc-Phe-Leu amide of (4S)-3-oxo-4-amino-2,2-difluoro-1-isopentylcarbonylamino-5-cyclohexylpentane Using the procedure of Example 88 with the resultant compound from Example 85 provided the desired product as a solid.

Analysis calculated for $C_{37}H_{58}F_2N_4O_6$: C, 64.14; H, 8.44; N, 8.09. Found: C, 63.84; H, 8.43; N, 7.89

EXAMPLE 95

Boc-Phe-Leu amide of (4S)-3-oxo-4-amino-2,2-difluoro-1-isopropylsulfonyl-5-cyclohexylpentane Using the procedure of Example 88 with the resultant compound from Example 86 provided the desired product as a solid.

Anal. calcd. for $C_{34}H_{53}F_2N_3O_7S$ 0.5H₂O: c, 58.77; H, 7.83; N, 6.05. Found: C, 58.85; H, 7.87; N, 5.90.

EXAMPLE 96

Boc-Phe-Leu amide of (Z,4S)-3-oxo-4-amino-2-fluoro-1-isopropylsulfonyl-5-cyclohexyl-1-pentene Using the procedure of example 88 with the resultant compound of Example 87 provided the desired product along with the corresponding E isomer, both as solids. Z isomer.

Anal. calcd. for $C_{34}H_{52}FN_3O_7S$ 0.5H₂O: C, 60.51; H, 7.92; N, 6.23. Found: C, 60.36; H, 7.79; N, 6.09. E isomer. NMR (300 MHz, CDCl₃, ppm): 6.34 (d, 1H, J=18 Hz).

EXAMPLE 97

Boc-His Amide of (3S, 4S)-4-Amino-3-hydroxy-6-methyl-1-phenethylsulfonyl-heptane Using the procedure of Example 22 with the resultant compound of Example 12 and Boc-His-OH rather than Boc-Phe-His-OH, gave the desired compound.

EXAMPLE 98

[(4-Morpholinyl)carbonyl]-Phe Methyl ester

A suspension of L-phenylalanine methyl ester hydrochloride (6 ) in toluene (125 ml) was heated to 100° C. while phosgene gas was bubbled into the reaction mixture. After approximately 1.5–2 h, the mixture became homogeneous. The passage of phosgene was continued for an additional 15 min, keeping the temperature at 90°–100° C. The toluene was then evaporated and the residue chased several times with benzene. A 6.5 g (0.03167 mol) sample of -isocyanato-L-phenylalanine methyl ester was dissolved in 50 ml of methylene chloride and cooled to 0° C. Morpholine (2.76 ml, 0.03167 mol) dissolved in 5 ml of methylene chloride was added dropwise. After 10 min at 0°–5° C., the reaction mixture was distributed between 0.5 N HCl and methylene chloride. The organic layer was washed with aqueous NaHCO$_3$ and dried over MgSO$_4$. Evaporation of the solvent gave 7 g of product after trituration with hexane, m.p. 90°–91° C.

EXAMPLE 99

[(4-Morpholinyl)carbonyl]-Phe-OH to a 0° C. solution of the product from Example 98 (3.63 mmol) in dioxane (15 ml) was added a solution of lithium hydroxide (0.174 g, 4.15 mmol) in water (7.5 ml). After stirring for 1 h at 0°–5° C., the reaction mixture was diluted with cold water and extracted 2X with ether. The aqueous portion was acidified with 6N HCl and extracted with ether. The organic extract was washed with brine and evaporated to give an 87% yield of product as a viscous liquid.

EXAMPLE 100

Boc-(Me)His Amide of (3S,4S)-4-Amino-3-hydroxy-6-methyl-1-phenethylsulfonyl heptane.

to a stirred solution of N -(t-butyloxycarbonyl)-N -methyl-N$^{im}$-tosyl-L-histidine [*J. Med. Chem.* 29, 2088 (1986), 9.15 mmol] and the product from Example 12 (6.1 mmol) in dichloromethane (75 ml) was added 1.28 ml (9.18 mmol) of triethylamine, followed by the slow addition of diethoxyphosphoryl cyanide (1.36 ml, 8.87 mmol). After being stirred at room temperature for 16 h, the reaction mixture was diluted with dichloromethane and then washed with saturated aqueous NaHCO$_3$. The organic phase was dried (MgSO$_4$) and then concentrated. The residue was chromatographed on silica gel eluting with ethyl acetate/hexane mixture to give a 75% yield of coupled product.

The above product was stirred in CH$_3$OH with 5 equiv. HOBT for 16 h. The reaction mixture was filtered. The filtrate was evaporated to solid which was taken up with CHCl$_3$, washed with dil NaHCO$_3$, brine, dried and filtered. The resultant residue after evaporation was chromatographed eluting with 5% CH$_3$Oh/CHCl$_3$. The desired product was obtained in 60% yield.

EXAMPLE 101

[(4-Morpholinyl)carbonyl]-Phe-(Me)His Amide of (3S,4S)-4-Amino-3-hydroxy-6-methyl-1-phenethylsulfonylheptane.

The product from Example 100 was deprotected with trifluoroacetic acid/methylene chloride (1:1) and the resultant amine coupled to the product from Example 99 using the method of Example 100. There was obtained a 50% yield of the title compound.

EXAMPLE 102

3-Benzyloxycarbonylamino-3-methylbutanoic Acid

A solution of 2,2-dimethyl-3-carbomethyoxypropionic acid [LeMaul, *Bull. Soc. Chim. Fr.*, 828 (1965), 20 g, 0.125 mol], diphenylphosphorylazide (34.3 g, 0.125 mol) and triethylamine was heated in toluene (150 ml) at 100° C. for 2 h. After cooling at 5° C., the toluene solution was washed successively with 0.5 M HCl, aqueous NaHCO$_3$ and brine. Evaporation of the dried solution gave a residue which was chromatographed on silica gel eluting with 60/40 hexane-ether. There was obtained 13 g of methyl 3-isocyanato-3-methylbutanoate as a mobile liquid. A solution of this material in toluene (20 mol) was treated with benzyl alcohol (13 ml) and the resulting mixture heated at reflux for 40 h. Evaporation of the toluene left a residue which was dissolved in methanol (125 ml) and then treated with a solution of NaOH (6.6 g, 0.165 mol) in 22 ml of water. After 5 h, the reaction mixture was partially evaporated, washed with ether and acidified with 6N HCl. Extraction with methylene chloride and evaporation gave 21 g of the desired product NMR (300 MHz, CDCl$_3$): 1.42 (s,6H), 2.78 (s,2H), 5.08 (s,2H).

EXAMPLE 103

Cbz-[(β,β-di-Me)-β-Ala]-Phe-OCH$_3$

A 4.0 g sample of 3-benzyloxycarbonylamino-3-methylbutanoic acid was coupled to phenylalanine methyl ester hydrochloride (3.43 g) using the mixed anhydride procedure described in Example 16. Purification of the crude product by flash chromatography eluting with 65/35 ether-hexane gave an 86% yield of product. NMR (300 MHz, CDCl$_3$): 1.32 (s,3H), 1.34 (s,3H), 2.46 (d,1H), 2.63 (d,1H), 2.98 (dd,1H), 3.09 (dd,1H), 3.70 (s,3H), 4.86 (dd,1H), 4.97 (d,1H), 5.2 (d,1H), 5.3 (s,1H), 6.13 (d,1H).

EXAMPLE 104

Cbz-[β,β-di-Me)-β-Ala]-Phe-OH

To a 0° C. solution of Cbz-[(β,β-di-Me)-β-Ala]-Phe-OMe (1.5 g, 3.63 mmol) in dioxane (15 ml) was added a solution of lithium hydroxide (0.174 g, 4.15 mmol) in water (7.5 ml). After stirring for 1 h at 0°–5° C., the reaction mixture was diluted with cold water and extracted 2× with ether. The aqueous portion was acidified with 6N HCl and extracted with ether. The organic extract was washed with brine and evaporated to give an 87% yield of product as a viscous liquid.

EXAMPLE 105

Cbz-[(β,β-di-Me)-β-Ala]-Phe-His Amide of (3S,4S)-4-Amino-3-hydroxy-6-methyl-1-phenethylsulfonylheptane The product from Example 104 was coupled to the product from Example 97 using the procedure described in Example 22. There was obtained a 50% yield of the title compound.

EXAMPLE 106

H-[(β,β-di-Me)-β-Ala]-Phe-His Amide of (3S,4S)-4-Amino-3-hydroxy-6-methyl-1-phenethylsulfonylheptane The resultant compound of Example 105 (0.2 g, 0.247 mmole) in acetic acid (5 ml) was hydrogenated at 1 atmosphere with 10% Pd/C (0.1 g) for 8 h. Filtration, extraction of the catalyst with acetic acid, and evaporation of the combined acetic acid solutions gave a residue which was dissolved in H₂O (10 ml) and lyopholized to provide 75% of the desired product.

EXAMPLE 107

3-Benzyloxycarbonylamino-2,2-dimethylpropionic Acid

3-Carbomethoxy-3-methylbutanoic acid [*Bull. Soc. Chim. Fr.*, 828 (1965), 7.85 g, 0.049 mol]was reacted with diphenylphosphorylazide and triethylamine as described in Example 102. After heating the toluene solution for 1.5 h, benzyl alcohol (8 g) was added directly to the reaction mixture and heating at reflux was continued for 20 h. Work-up and chromatography gave methyl 3-benzyloxycarbonylamino-2,2-dimethylpropionate. NMR (300 MHz, CDCl₃): 1.2 (s,6H), 3.3 (d,2H), 3.68 (s,3H), 5.1 (s,2H), 5.22 (m,1H). A sample of the methyl ester (6.21 g, 0.023 mol) was saponified with 3.1 g (0.78 mol) of NaOH in 100 ml ethanol/10 ml H₂O at room temperature for 48 h. Work-up as in Example 102 gave the desired product as a liquid. NMR (300 MHz, CDCl₃): 1.23 (s,6H), 3.32 (d,2H), 5.10 (s,2H), 5.27 (m,1H).

EXAMPLE 108

Cbz-[(α,α-di-Me)-β-Ala]-(OMe)Tyr-OCH₃

To a solution of 3-benzyloxycarbonylamino-2,2-dimethylpropionic acid (1.5 g, 5.97 mmol) in methylene chloride (13 ml) was added oxalyl chloride (0.757 g, 5.97 mmol) and dimethylformamide (30 ul). After stirring for 1 h at room temperature, the reaction mixture was cooled to 0° C. and treated successively with OMe-tyrosine methyl ester hydrochloride (1.465 g, 5.97 mmol) and N-methylmorpholine (1.81 g, 17.9 mmol). Stirring for 1 h at 0°-5° C. was followed by distribution between CH₂Cl₂ and 0.5 N HCl. The organic phase was washed with aqueous NaHCO₃ and brine and dried over MgSO₄. Evaporation of the solvent gave a residue which was purified by chromatography. There was obtained a 61.5% yield of product as a liquid.

EXAMPLE 109

Cbz-[(α,α-di-Me)-β-Ala]-(OMe)Tyr-OH

To a 0° C. solution of Cbz-[(α,α-di-Me)-beta (OMe)-Tyr-OMe (1.2 g, 2.71 mmol) in dioxane (15 ml) was added a solution of lithium hydroxide (0.115 g, 2.75 mmol) in water (7.5 ml). After stirring for 1 h at 0°-5° C., the reaction mixture was diluted with cold water and extracted 2X with ether. The aqueous portion was acidified with 6N HCl and extracted with ether. The organic extract was washed with brine and evaporated to give an 87% yield of product as a viscous liquid.

EXAMPLE 110

H-[(α,α-di-Me)-β-Ala]-(OMe)Tyr-His Amide of (3S,4S)-4-Amino-3-hydroxy-6-methyl-1-phenethylsulfonylheptane Using the procedures described in Examples 105 and 106, the product from Example 109 was converted to the desired product.

EXAMPLE 111

2(S)-[[(4-Morpholinyl)carbonyl]oxy]-3-phenylpropionic Acid Methyl ester

To L-phenyllactic acid methyl ester (3.2 g) was added 150 ml of 12% phosgene in toluene and 25 drops of dimethylformamide. After stirring for 16 h at room temperature, the solvent was evaporated and the residue chased several times with benzene. The resulting product was dissolved in methylene chloride (50 ml), cooled to 9° C. and treated by dropwise addition with 3.86 g (0.44 mol) of morpholine. The reaction mixture was stirred for 2 h at 0°-5° C. and then distributed between 0.5 N HCl and methylene chloride. The organic phase was washed with aqueous NaHCO₃ and brine and evaporated to a residue. Flash chromatography on silica gel eluting with 2/1 ether-hexane gave a 65% yield of product. NMR (300 MHz): 3.08 (dd,1H), 3.20 (dd,1H), 3.8 (s,3H), 5.19 (dd,1H).

EXAMPLE 112

2(S)-[(4-Morpholinyl)carbonyl]oxy-3-phenylpropionic acid

Using the hydrolysis procedure of Example 99, the title compound was obtained in 90% yield.

EXAMPLE 113

2(S)-[(Morpholinyl)carbonyl]oxy-3-phenylpropionyl-His Amide of (3S,4S)-4-Amino-3-hydroxy-6-methyl-1-phenethylsulfonylheptane Using the procedure of Example 22 with the resultant compound of Example 97 and the product from Example 112 rather than Boc-Phe-His-OH, gave the desired product.

EXAMPLE 114

Ethyl hydrogen (α,α-dimethylbenzyl)malonate

Diethyl (α, α -dimethylbenzyl)malonate was prepared by the conjugate addition of phenyl magnesium bromide to diethyl isopropylidenemalonate as described by C. Holmberg [*Liebigs Ann. Chem.*, 748 (1981)]. A solution of this diester (42.1 g, 0.15 mol) in ethanol (100 ml) was treated by dropwise addition with a solution of potassium hydroxide (8.48 g, 0.13 mol) in 100 ml of ethanol. After heating at 90° C. for 1 h and at 50° C. for 20 h, the reaction mixture was evaporated on the rotary evaporator to a residue. The residue was diluted with water and extracted with ether to remove unreacted starting material. The aqueous phase was cooled to 5° C., acidified to pH 3 with 6N HCl, and extracted with methylene chloride. The organic layer was washed with brine solution and dried over magnesium sulfate. Evaporation of the solvent gave 27.3 g (84%) of liquid product. NMR (CDCl₃): 1.05 (3H,t), 1.6 (6H,s), 3.78 (1H,s), 3.96 (2H,m), 7.2–7.4 (5H,m).

EXAMPLE 115

Ethyl 2(R,S)-[[(4-morpholinyl)carbonyl]amino]-3,3-dimethyl-3-phenylpropionate

To a solution of ethyl hydrogen (α, α-dimethylbenzyl)malonate (4 g, 0.016 mol) in toluene was added triethylamine (2.33 ml, 0.016 mol) and diphenylphosphoryl azide (4.4 g, 0.016 mol). The reaction mixture was heated at 100° C. for 2.5 h, cooled to 5° C., and treated with 1.4 ml (0.016 mol) of morpholine. After stirring overnight at room temperature, the toluene solution was washed successively with 1N HCl and aqueous sodium bicarbonate solution. The dried organic solution was evaporated to a residue which was purified by column chromatography on silica gel. There was obtained 3.7 g (69%) of product after trituration with hexane, mp 93°–94° C.

Anal. Calcd. for $C_{18}H_{26}N_2O_4$: c, 64.55; H, 7.84; N, 8.38. Found: C, 64.72; H, 7.95; N, 8.33.

EXAMPLE 116

2(R,S)-[[(4-Morpholinyl)carbonyl]amino]-3, 3-dimethyl-3-phenylpropionic acid

A solution of the product from Example 115 (2 g, 5.99 mmol) in dioxane (10 ml) was treated with 0.26 g (6.5 mmol) of sodium hydroxide in 5 ml of water. After stirring for 16 h at 35° C., the reaction was worked up as described in Example 114 to give a 93% yield of product.

EXAMPLE 117

2(R,S)-[[(4-Morpholinyl)carbonyl]amino]-3,3-dimethyl-3-phenylpropionyl-His Amide of (3S,4S)-4-Amino-3-hydroxy-6-methyl-1-phenethylsulfonylheptane Using the procedure of Example 22 with the resultant compound of Example 97 and the product from Example 116 rather than Boc-Phe-His-OH, gave the desired product.

EXAMPLE 118

4(S)-t-Butyloxycarbonylamino-5-cyclohexyl-3(R,S)-hydroxyl-1-pentene

To a stirred −78° C. solution of Boc-cyclohexylalanine methyl ester (10.2 g, 35.8 mmol) in dry toluene (60 ml) was added diisobutylaluminum hydride (34 ml of a 1.5 M solution in toluene). After 30 min, vinyl magnesium bromide (108 ml of 1 M solution in tetrahydrofuran (THF)) was added. After stirring for 15 h at 0° C., the mixture was carefully quenched with methanol, treated with Rochelle salts (22 ml of saturated aqueous solution in 140 ml $H_2O$), and filtered. After extracting the solids 5 times with ethyl acetate, the extracts and filtrate were combined and the organic phase was washed with brine, dried, filtered and evaporated to an oil (10.2 g). Chromatography on silica gel eluting with hexane/ethyl acetate mixtures provided 6.1 g (60%) of the desired product.

Anal. Calcd. for $C_{16}H_{29}NO_3 \cdot H_2O$: C, 66.8; H, 10.3; H, 4.9. Found: C, 66.9; H, 10.2; N, 4.7.

EXAMPLE 119

4(S)-Cyclohexylmethyl-5(R,S)-vinyl-2-oxazolidinone

The resultant product of Example 118 (2.80 g, 9.88 mmol) in dry dimethylformamide (DMF) (50 ml) was added to a stirred suspension of NaH (593 mg of a 60% dispersion in oil, 14.8 mmol, hexane washed) in dry DMF (50 ml). After 3 h, the mixture was quenched (750 ml water+100 m brine) and extracted with ether (5×100 ml). The combined organic phase was washed with brine (3×50 ml), dried (MgSO$_4$), filtered and evaporated to an oil (2.33 g). The NMR spectrum of the crude product revealed an 82:18 mixture of 5S:5R diastereomers. Silica gel chromatography gave 80% recovery of pure diastereomers. 5S:

Anal. Calcd. for $C_{12}H_{19}NO_2$: C, 68.9; H, 9.1; N, 6.7. Found: C, 68.4; H, 9.2; N, 6.5 Mass spectrum: (M+1)$^+$=210. 5R: Mass spectrum: (M+1)$^+$=210.

EXAMPLE 120

(3S,4S)-3-Hydroxy-4-amino-5-cyclohexyl-1-pentene

To the resultant 5S-diasteriomer from Example 119 (2.06 g, 9.84 mmol) in dioxane (180 ml) and water (120 ml) was added barium hydroxide octahydrate (6.24 g, 19.8 mmol). The mixture was refluxed for 18 h, cooled, filtered, concentrated, taken up on water and extracted with ethyl acetate which was dried over Na$_2$SO$_4$ and evaporated to afford 1.64 g (91%) of the desired product, mp: 59°–61° C.

Anal. Calcd. for $C_{11}H_{21}NO$: C, 72.08; H, 11.55; N, 7.64. Found: C, 71.67; H, 11.68; N, 7.36.

EXAMPLE 121

(3S,4S)-3-Hydroxy-4-tert-butoxycarbonylamino-5-cyclohexyl-1-pentene

To the resultant compound from Example 120 (1.62 g, 8.84 mmol) in methylene chloride (20 ml) was added di-tert-butyldicarbonate (1.93′ g, 8.84 mmol). The mixture was stirred for 14 h, diluted with ethyl acetate, washed sequentially with 0.5 M H$_3$PO$_4$, saturated NaHCO$_3$ solution and brine, then dried over Na$_2$SO$_4$ and evaporated to afford 2.51 g (100%) of the desired compound.

EXAMPLE 122

(3S,4S)-1,3-Dihydroxy-4-t-butyloxycarbonylamino-5-cyclohexylpentane

The resultant compound from Example 121 (327.6 mg, 1.16 mmol) in tetrahydrofuran (THF, 2 ml) at 0° C. was treated with 9-borabicyclo(3.3.1)nonane (4.6 ml, 2.2 mmol in THF). After 3 h at room temperature water (0.1 ml) then NaOH (280 mg, 7.0 mmol) in water (1 ml) then 30% H$_2$O$_2$ (0.70 ml, 6.9 mmol) were added and the mixture was heated at 50° C. for 90 min. The mixture was concentrated, dissolved in ethyl acetate, washed with brine, dried over Na$_2$SO$_4$, evaporated and chromatographed on silica gel with 2% methanol in chloroform to give 351.1 mg (100%) of the desired compound as an oil. DCI-MS: (M+H)=302.

EXAMPLE 123

(3S,4S)-1-Mesyloxy-3-hydroxy-4-t-butyloxycarbonylamino-5-cyclohexylpentane

The resultant compound from Example 122 was reacted according to the procedure in Example 72 to give the desired compound. EI-Ms: M$^+$=379.

EXAMPLE 124

(3S,4S)-1-Azido-3-hydroxy-4-t-butyloxycarbonylamino-5-cyclohexylpentane

The resultant compound from Example 123 was reacted according to the procedure in Example 73 to give the desired compound. DCI-MS: (M+H)=327.

EXAMPLE 125

Boc-Phe-His Amide of (3S,4S)-1-Azido-3-hydroxy-4-amino-5-cyclohexylpentane

Using the procedure of Example 35 with the resultant compound from Example 124 gave the desired compound.

Anal. Calcd. for $C_{31}H_{46}N_8O_5 \cdot 0.5\ H_2O$: C, 60.08; H, 7.64; N, 18.08. Found: C, 60.35; H, 7.48; N, 17.75.

EXAMPLE 126

α-Isocyanato-L-(O-methyl)tyrosine

A suspension of (O-methyl)tyrosine methyl ester hydrochloride (6 g) in toluene (125 ml) was heated at 100° C. while phosgene was bubbled into the reaction mixture. After 2 h the mixture became homogeneous and the phosgene was continued for an additional 15 min. The mixture was cooled and evaporated with several benzene chasers to provide the desired product.

EXAMPLE 127

1-Benzyloxycarbonylamino-2,3-propanediol

1-Amino-2,3-propanediol (15.2 g, 167 mmol) and NaOH (8.1 g, 204 mmol) in water 70 ml) at −10° C. was treated dropwise with benzyl chloroformate (28.5 ml, 200 mmol) to ether (30 ml) over 20 min. The reaction was stirred at 0° C. for 30 min then at room temperature for 2 h. The mixture was acidified with 2 M HCl and extracted with ethyl acetate which was washed with 0.5 M $H_3PO_4$ and brine, then dried over $Na_2SO_4$ and evaporated. Recrystallization of the residue from benzene afforded 16.59 g (44%) of the desired product as a white powder. NMR (300 MHz, $CD_3OD$, ppm): 3.12 (dd,1H), 3.28 (dd,1H), 3.50 (m, 2H), 3.68 (m, 1H), 5.08 (s,2H), 7.35 (m, 5H).

EXAMPLE 128

1-Methylamino-2,3-propanediol

Lithium aluminum hydride (7.20 g, 189 mmol) in tetrahydrofuran (THF, 300 ml) was heated to reflux and the resultant compound from Example 127 (17.0 g, 75.5 mmol) in THF (150 ml) was added dropwise over 10 min. The mixture was refluxed for 2 h, cooled, quenched sequentially with water (10 ml), 3 M NaOH (40 ml) and water (20 ml), then filtered and concentrated. The residue was dissolved in water which was washed with ether and evaporated. Bulb to bulb distillation of the residue afforded 2.0 g (25%) of the desired compound as an oil. NMR (300 MHz, $CDCl_3$, ppm): 2.45 (S,3H), 2.68 (dd,1H), 2.77 (dd,1H), 3.61 (dd,1H), 3.72 (dd,1H), 3.78 (M,1H).

EXAMPLE 129

(N-Methyl-2,3-dihydroxypropylamino)carbonyl-(O-methyl)tyrosine methyl ester

To the resultant compound from Example 126 (1.53 g, 6.5 mmol) in dioxane (5 ml) at 0° C. was added the resultant compound from Example 128 (0.684 g, 6.5 mmol). The reaction was stirred at 0° C. for 1 h and then at room temperature for 1 h, evaporated and chromatographed on silica gel with 5% methanol in chloroform to afford 1.855 g (84%) of the desired product as an oil. NMR (300 MHz, $CDCl_3$, ppm), 2.88, 2.89 (S,3H total), 3.05 (m,2H), 3.26–3.60 (m,5H), 3.73 (S,3H), 3.80 (S,3H), 4.70 (m,1H), 5.07 (broad t,1H), 6.83 (dd,1H), 7.02 (dd,1H).

EXAMPLE 130

(N-Methyl-2,3-dihydroxypropylamino)carbonyl-(O-methyl)tyrosine

The resultant compound from Example 129 (114 mg, 0.355 mmol) in dioxane (4 m) and water (2 ml) at 0° C. was treated with LiOH monohydrate (42.0 mg, 1 mmol). After 90 min 2 M HCl (0.6 ml, 2.3 mmol) was added and the mixture was evaporated to a foam which was used without further purification; DCI-MS: $(M+H)^+ = 327$.

EXAMPLE 131

Dimethylaminocarbonyl-(O-methyl)tyrosine methyl ester

Prepared from dimethyl amine and the resultant compound from Example 126 according to the procedure for Example 129.

EXAMPLE 132

Dimethylaminocarbonyl-(O-methyl)-tyrosine

Prepared according to the procedure of Example 130 from the resultant compound of Example 131 with the modification that the product was isolated by pouring the reaction mixture into 2 M HCl and extracting with ethyl acetate which was dried over $Na_2SO_4$ and evaporated. EI-MS: $M^+ = 266$.

Anal. Calcd. for $C_{13}H_{18}N_2O_4$: C, 58.64; H, 6.81; N, 10.52. Found: C, 58.44; H, 6.87; N, 9.95.

EXAMPLE 133

3,3-Dimethylglutaric Acid Mono t-butyl ester 3,3-Dimethylglutaric anhydride (455 mg, 3.2 mmol) in tetrahydrofuran (THF, 5 ml) was treated with sublimed potassium t-butoxide (395 mg, 3.5 mmol). After 30 min the solution was concentrated, poured into saturated $NaHCO_3$ solution and washed with ether. The aqueous phase was acidified to pH 4 with 0.5 M $H_3PO_4$ and extracted with chloroform which was dried over $Na_2SO_4$ and evaporated to afford 179 mg (26%) of the desired product as an oil. NMR (300 MHz, $CDCl_3$, ppm), 1.13 (s,6H), 1.47 (s,9H), 2.33 (s,2H), 2.45 (s,2H).

EXAMPLE 134

(4-t-Butyloxycarbonyl-3,3-dimethyl) butanoylphenylalanine benzyl ester

Prepared according to the procedure from Example 16 from the resultant compound from example 133 and phenylalanine benzyl ester p-toluenesulfonic acid salt. NMR (300 MHz, $CDCl_3$, ppm), 0.96 (s,3H), 1.00 (s,3H), 1.44 (s,9H), 1.90 (d,1H), 2.16 (d,1H), 2.25 (d,1H), 2.29 (d,1H), 3.03 (dd,1H), 3.17 (dd,1H), 4.92 (m, 1H), 5.12 (d,1H), 5.16 (d,1H), 7.10–7.40 (m,10H).

EXAMPLE 135

4-t-Butyloxycarbonyl-3,3-dimethyl)butanoylphenylalanine

The resultant compound from Example 134 and an equal weight of 10% Pd on carbon in methanol were stirred under a hydrogen atmosphere for 3 h. The reaction was filtered and evaporated to provide the desired product as an oil. NMR (300 MHz, $CDCl_3$, ppm), 0.93 (s,3H), 0.99 (s,3H), 1.45 (s,9H), 1.77 (d,1H), 2.10 (d,1H), 2.19 (d,1H), 2.25 (d,1H), 3.02 (dd,1H), 3.33 (dd,1H), 4.72 (m,1H), 7.25 (m,5H).

EXAMPLE 136

(Dimethylaminocarbonyl (O-methyl)Tyr-His Amide of (3s,4S)-1-(3-Methylbutylcarbonylamino)-3-hydroxy-4-amino-5-cyclohexylpentane Using the procedure of Example 35 with the resultant compounds from Example 132 and Example 36 gave the desired compound.

EXAMPLE 137

(N-Methyl-2,3-dihydroxypropylamino)carbonyl(O-methyl) Tyr-His Amide of (3s,4S)-1-(3-Methyl-butylcarbonylamino)-3-hydroxy-4-amino-5-cyclohexylpentane Using the procedure of Example 35 with the resultant compounds from Example 129 and Example 36 gave the desired compound.

EXAMPLE 138

(4-t-Butyloxycarbonyl-3,3-dimethyl)butanoyl-Phe-His Amide of (3S,4S)-1-(3-Methyl-butylcarbonylamino)-3-hydroxy-4-amino-5-cyclohexylpentane Using the procedure of Example 35 with the resultant compounds from Example 135 and Example 36 gave the desired compound.

EXAMPLE 139

(4-Hydroxycarbonyl-3,3-dimethyl)butanoyl-Phe-His Amide of (3-Methylbutylcarbonylamino)-3-hydroxy-4-amino-5-cyclohexylpentane HCl Salt The resultant compound from Example 136 was stirred in 4 M HCl/methanol for 1 h and then evaporated to provide the desired compound.

EXAMPLE 140

(4R)-3-(3-Phenylpropionyl)-4-(2-propyl)-oxazolidine-2-one

To a stirred solution of 4-(2-propyl)-oxazolidine-2-one in anhydrous tetrahydrofuran (250 ml) under a nitrogen atmosphere at −78° C. were added in a dropwise fashion a solution of n-butyllithium in hexane (50 ml, 77.4 mmol) over 5 to 10 min. After stirring an additional 20 min at −78° C. 3-phenylpropionyl chloride (12.7 ml, 85.2 mmol) was added neat. The reaction was warmed to room temperature and stirred 1 to 2 h at the temperature. The reaction was quenched by adding 100 ml of saturated aqueous ammonium chloride and the volatiles removed by rotary evaporation. The resulting aqueous residue was extracted three times with ether and the combined organic phases were washed with brine, dried ($Na_2SO_4$), filtered and concentrated in vacuo. Recrystallization from hexanes/ethyl acetate provided the title compound (16.6 g, 82%). m.p.=86.5 to 87.5° C. Mass spectrum: $(M+NH_4)^+=279$, $(M+H)^+=262$.

EXAMPLE 141

(4R)-3-[(2R)-3-t-butoxycarbonyl-2-benzylpropionyl]-4-(2-propyl)-oxazolidine-2-one To a stirred solution of the product resulting from Example 140 (2.28 g, 8.72 mmol), in anhydrous tetrahydrofuran (30 ml) under a nitrogen atmosphere at −78° C. was added a solution of sodium hexamethyldisilylamide (9.6 ml, 9.59 mmol) in tetrahydrofuran. After stirring for 30 min at −78° C., t-butyl bromoacetate (2.21 g, 11.34 mmol) was added in anhydrous tetrahydrofuran and the resulting solution stirred 1 h at −78° C. The reaction was quenched by adding 20 ml of saturated aqueous ammonium chloride and then partitioned between water and ether. The aqueous layer was drawn off and extracted with ether. The combined organic phases were washed with 10% aqueous HCl, saturated aqueous $NaHCO_3$, and brine, dried ($Na_2SO_4$), filtered, and concentrated in vacuo. Recrystallization from acetone/hexanes provided the desired purified product (2.59 g, 79%). mp=167°–168° C. Mass spectrum: $(M+NH_4)^+=393$, $(M+H)^+=376$.

EXAMPLE 142

Benzyl-(2R)-3-(t-butoxycarbonyl)-2-benzyl-propionate

To a stirred solution of dry benzyl alcohol (0.55 ml, 5.33 mmol) in anhydrous tetrahydron furan (18 ml) under a nitrogen atmosphere at 0° C. was added a hexane solution of n-butyllithium (2.58 ml; 4.00 mmol). To this solution was added the product from Example 141 in anhydrous tetrahydrofuran (10 ml). After stirring 1 h at 0° C. the reaction was quenched by adding excess saturated aqueous ammonium chloride. The volatiles were removed by rotary evaporation and the resulting aqueous residue extracted two times with ether. The combined organic layers were washed with brine, dried ($Na_2SO_4$), filtered, and concentrated in vacuo provided an oil which was purified by chromatography on $SiO_2$ (15% ether acetate/hexanes) to provide the desired product (0.89 g, 94%) as a colorless oil. Mass spectrum: $(M)^+=354$.

EXAMPLE 143

Benzyl-(2R)-3-carboxy-2-benzylpropionate

The product of Example 142 (0.52 g, 1.47 mmol) was dissolved in a 1:1 (v:v) solution (6 ml) of trifluoroacetic acid and dichloromethane and stirred at room temperature for 1 h. The volatiles were removed in vacuo to provide the title compound (0.437 g, 100%) as an oil which crystallized on standing. The unpurified material was of sufficient purity to employ in subsequent steps. Mass spectrum: $(M)^{30}=298$.

EXAMPLE 144

(2R)-3-(N-methyl-2,3-dihydroxypropylamino)carbonyl-2-benzylpropionic Acid Benzyl ester Prepared according to the procedure for Example 16 from the resultant compounds of Example 128 and Example 143 NMR (300 MHz, $CDCl_3$, ppm), 3.00 (s,3H), 5.10 (m,2H), 7.10–7.40 (m,10H); Ei-MS: $M^+=385$.

EXAMPLE 145

(2R)-3-(N-Methyl-2,3-dihydroxypropylamino) carbonyl-2-benzylpropionic Acid

The resultant compound from Example 144 (200 mg, 0.523 mmol) and 10% Pd on carbon (200 mg) in methanol (10 ml) were stirred under a hydrogen atmosphere for 3 h. The reaction was filtered and evaporated to afford 148 mg (97%) of the desired product as an oil.

Anal. Calcd. for $C_{15}H_{21}NO_5 \cdot 0.25\ H_2O$: C,60.09; H, 7.23; N, 4.67. Found: C, 59.76; H, 7.10; N, 4.45.

EXAMPLE 146

(2R)-3-(N-Methyl-2,3-dihydroxypropylamino)carbonyl-2-benzylpropionyl-His Amide of(3S,4S)-1-(3Methylbutylcarbonylamino)-3-hydroxy-4-amino-5-cyclohexylpentane Using the procedure of Example 35 with the resultant compounds from Example 145 and Example 36 gave the desired compound.

EXAMPLE 147

Boc-Leu Amide of (3S,4S)-1-(3-Methylbutylcarbonylamino)-3-hydroxy-4-amino-5-cyclohexylpentane Using the procedure of Example 34 and employing Boc-Leu-OH rather than Boc-Phe-Ala-OH gave the desired compound.

EXAMPLE 148

Boc-1-Nal-Leu Amide of (3S,4S)-1-(3-Methylbutylcarbonylamino)-3-hydroxy-4-amino-5-cyclohexylpentane Using the procedure of Example 34 with the resultant compound from Example 147 and using Boc-1-napthylalanine (Boc-1-Nal) rather than Boc-Phe-Ala-OH provided the desired compound.

EXAMPLE 149

(3S,4S,7R,9S,10S)-1-(3-Methylbutylcarbonylamino)-3,9-dihydroxy-4-cyclohexylmethyl-5-aza-6-oxo-7-(4-pentenyl)-10-(t-butyloxycarbonylamino)-11-phenylundecane Using the procedure of Evans, et al. (*J. Org. Chem.* 1985, 50, 4615) with the resultant compound of Example 33 which had been deprotected as described in Example 34 and (3R,5S,1'S)-5-(1-t-butyloxycarbonylamino-2-phenylethyl)-3-(4-pentenyl)dihydrofuran-2-(3H)-one (D. J. Kempf, *J. Org. Chem.* 1986, 51, 3921) gave the desired compound.

EXAMPLE 150

Cbz-D-Ala-Phe-His Amide of (3S,4S)-1-(3-Methylbutylcarbonylamino)-3-hydroxy-4-amino-5-cyclohexylpentane Using the procedure of Example 37, but replacing Bba with Cbz-D-Ala-Phe-OH gave the desired product.

EXAMPLE 151

D-Ala-Phe-His Amide of (3S,4S)-1-(3-Methylbutylcarbonylamino)-3-hydroxy-4-amino-5-cyclohexylpentane The resultant compound of Example 150 (1.0 g) in glacial acetic acid (20 ml) was hydrogenated with 10% Pd/C (450 mg) at 55 p.s.i. $H_2$. After 3 h, the mixture was filtered and evaporated. The residue was partitioned between ethyl acetate and saturated aqueous $NaHCO_3$ for 30 min. The organic phase was washed (brine), dried ($Na_2SO_4$), filtered, and evaporated to give the desired compound in 78% yield.

EXAMPLE 152

($OCH_3$)Tyr-His Amide of (3S,4S)-1-(3-Methylcarbonylamine)-3-hydroxy-4-amino-5-cyclohexylpentane Following the procedures of Examples 150 and 151, but replacing Cbz-D-Ala-Phe-OH with Cbz-($OCH_3$)-TyrOH, gave the desired product.

EXAMPLE 153

(Imidazol-4-yl)acetyl-($OCH_3$)Tyr-His Amide of (3s,4S)-1-(3-Methylbutylcarbonyl amino)-3-hydroxy-4-amino-5-cyclohexylpentane Using the coupling procedure of Example 22 with (imidazol-4-yl)acetic acid and the resultant product of Example 152 gave the desired product.

EXAMPLE 154

(Imidazol-1-yl)acetyl-($OCH_3$)Tyr-His Amide of (3S,4S)-1-(3-Methylbutylcarbonylamino)-3-hydroxy-4-amino-5-cyclohexylpentane The resultant compound of Example 152 (126 mg) in dry THF at 0° C. was treated sequentially with 2 eq. N-methylmorpholine and 1 eq. bromoacetyl bromide. After 1 h, imidazole (5 eq.) was added. The mixture was warmed to room temperature for 6 h and then evaporated. Chromatography of the residue on silica gel (dichloromethane/isopropylamine/methanol) mixtures provided the desired product.

EXAMPLE 155

N-(2,3-dihydroxypropyl)Gly-($OCH_3$)Tyr-His Amide of (3S,4S)-1-(3-Methylbutylcarbonyl amino)-3-hydroxy-4-amino-5-cyclohexylpentane Following the procedure of Example 154, but replacing imidazole with 1-amino-2,3-dihydroxypropane provided the desired product.

EXAMPLE 156

(N-Butyl,4-$OCH_3$)Phenylalanine

To a stirred 0° C. suspension of (4-$OCH_3$)-phenylalanine (1.00 g, 5.12 mmol) and butyraldehyde (0.406 g, 110 M%) in methanol (10 ml) was added sodium cyanoborohydride (241 mg, 75M%). The mixture was warmed to room temperature for 23 and filtered. The solid was washed with methanol and suction dried to give 1.07 g (83%) of the desired product. Mass spectrum: $M^+ = 251$.

Ala. Calcd. for $C_{15}H<NO_3l/3H_2O$: C, 66.3; H, 8.5; N, 5.4. Found: C, 65.1; H, 8.3; N, 5.6.

EXAMPLE 157

(N-Butyl, 4-$OCH_3$)Phe-His Amide of (3S,4S)-1-(3-Methylbutylcarbonyl amino)-3-hydroxy-4-amino-5-cyclohexylpentane Using the coupling procedure of Example 37, but replacing Dba with the resultant product of Example 155, gave the desired product.

The compounds of the present invention can be used in the form of salts derived from inorganic or organic acids. Included among such salts are the following: acetate, adipate, alginate, aspartate, benzoate, benzenesulfonate, bisulfate, butyrate, citrate, camphorate, cyclopentanepropionate, fumarate, digluconate, camphorsulfonate, dodecylsulfate, ethanesulfonate, glucoheptanoate, glycerophosphate, hemisulfate, heptonate, hexanoate, hydrochloride, hydrobromide, hydroiodide, 2-hydroxyethanesulfonate, lactate, maleate, methanesulfonate, oxalate, pamoate, 2-naphthalenesulfonate, nicotinate, pectinate, picrate, persulfate, 3-phenylpropionate, pivalate, propionate, succinate, tartrate, thiocyanate, tosylate, and undecanoate. Also, the basic nitrogen-containing groups can be quaternized with such agents as loweralkyl halides, such as methyl, ethyl, propyl and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The novel compounds of the present invention possess an excellent degree of activity and specificity in treating renin-associated hypertension in a host. The ability of the compounds of the invention to inhibit human renal renin can be demonstrated in vitro by reacting a selected compound at varied concentrations with human renal renin, free from acid proteolytic activity, and with human renin substrate (angiotensinogen) at 37° C. and pH 6.0. At the end of the incubation, the amount of angiotensin I formed is measured by radioimmunoassay and the molor concentration required to cause 50% inhibition, expressed as the IC$_{50}$, is calculated. When tested in accordance with the foregoing procedure, the compounds of the invention demonstrated IC$_{50}$'s in the range of $10^{-6}$ to $10^{-9}$ M as seen in Table I.

TABLE I

| EXAMPLE NO. | ACTIVITY - IC$_{50}$(M) |
| --- | --- |
| Example 16 | $4 \times 10^{-6}$ |
| Example 17 | $5.5 \times 10^{-6}$ |
| Example 18 | $2 \times 10^{-6}$ |
| Example 19 | $2.5 \times 10^{-6}$ |
| Example 21 | $2 \times 10^{-6}$ |
| Example 22 | $1 \times 10^{-7}$ |
| Example 23 | $8 \times 10^{-8}$ |
| Example 30 | $2.5 \times 10^{-6}$ |
| Example 34 | $3 \times 10^{-8}$ |
| Example 35 | $1.5 \times 10^{-8}$ |
| Example 42 | (41% inhibition at $10^{-5}$ M) |
| Example 44 | $2 \times 10^{-6}$ |
| Example 46 | $3 \times 10^{-6}$ |
| Example 50 | $2.5 \times 10^{-8}$ |
| Example 52 | $1.5 \times 10^{-8}$ |
| Example 53 | $1.5 \times 10^{-8}$ |
| Example 58 | $6 \times 10^{-9}$ |
| Example 59 | $1 \times 10^{-8}$ |
| Example 62 | $2 \times 10^{-8}$ |
| Example 67 | $2.5 \times 10^{-8}$ |
| Example 68 | $2 \times 10^{-8}$ |
| Example 78 | $3 \times 10^{-8}$ |
| Example 83(A) | $2.5 \times 10^{-8}$ |
| Example 83(B) | $5 \times 10^{-8}$ |
| Example 85 | $2 \times 10^{-8}$ |
| Example 86 | $1 \times 10^{-8}$ |
| Example 87 | $4.5 \times 10^{-9}$ |
| Example 88 | $2.5 \times 10^{-9}$ |
| Example 93 | $2.5 \times 10^{-9}$ |
| Example 94 | $2 \times 10^{-9}$ |
| Example 95 | $1 \times 10^{-9}$ |
| Example 96 | $2 \times 10^{-8}$ |
| Example 125 | $2 \times 10^{-8}$ |

The total daily dose administered to a host in single or divided doses may be in amounts, for example, from 0.001 to 10 mg/kg body weight and more usually 0.01 to 1 mg. Dosage unit compositions may contain such amounts or submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of the present invention may be administered orally, parenterally, by inhalation spray, rectally or topically in dosage unit formulations containing conventional nontoxic pharmaceutically acceptable carriers, adjuvants and vehicles as desired. The term parenteral as used herein includes subcutaneous injections, intravenous, intramuscular, intrasternal injection or infusion techniques.

Injectable preparation, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

Suppositories for rectal administration of the drug can be prepared by mixing the drug with a suitable nonirritating excipient such as cocoa butter and polyethylene glycols which are solid at ordinary temperatures but liquid at the rectal temperature and will therefor melt in the rectum and release the drug.

Solid dosage forms for oral administration may include capsules, tablets, pills, powders and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration may include pharmaceutically acceptable emulsions, syrups, solutions, suspensions and elixirs containing inert diluents commonly used in the art, such as water. Such compositions may also comprise adjuvants, such as wetting agents, emulsifying and suspending agents, and sweetening, flavoring and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

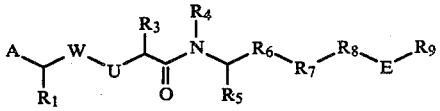

wherein A is hydrogen; loweralkyl; arylalkyl; $OR_{10}$ or $SR_{10}$ wherein $R_{10}$ is hydrogen, loweralkyl or aminoalkyl; $NR_{11}R_{12}$ wherein $R_{11}$ and $R_{12}$ are independently selected from hydrogen, loweralkyl, aminoalkyl, cyanoalkyl and hydroxyalkyl;

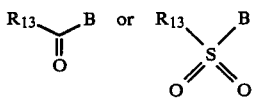

wherein B is NH, alkylamino, S, O, $CH_2$ or CHOH and $R_{13}$ loweralkyl, cycloalkyl, aryl, arylalky, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, (dihydroxyalkyl)(alkyl)amino, aminoalkyl, alkoxycarbonylalkyl, carboxyalkyl, N-protected aminoalkyl, alkylaminoalkyl, (N-protected)(alkyl)aminoalkyl, dialkylaminoalkyl, (heterocyclic)alkyl or a substituted or unsubstituted heterocyclic; W is C or CHOH and U is $CH_2$ or $NR_2$ with the proviso that when W is CHOH then U is $CH_2$; $R_1$ is loweralkyl, cycloalkylmethyl, benzyl, α, α -dimethylbenzyl, 4-methoxybenzyl, halobenzyl, (1-naphthyl)methyl, (2-naphthyl)methyl, (4-imidazolyl)-methyl, phenethyl, phenoxy, thiophenoxy or anilino; provided if $R_1$ is phenoxy, thiophenoxy or anilino, B is $CH_2$ or CHOH or A is hydrogen; $R_3$ is loweralkyl, vinylloweralkyl, benzyl or heterocyclic ring-substituted methyl; $R_5$ is loweralkyl, cycloalkylmethyl or benzyl; $R_2$ and $R_4$ are independently selected from hydrogen and loweralkyl; $R_6$ is CHOH or CO; $R_7$ is $CH_2$, $CF_2$ or CF with the proviso that when $R_6$ is CO, $R_7$ is $CF_2$; $R_8$ is $CH_2$, $CHR_{14}$ wherein $R_{14}$ is loweralkyl, cycloalkyl, cycloalkylalkyl, aryl or arylalkyl, or $R_7$ and $R_8$ taken together can be

with the proviso that when $R_7$ is $CF_2$, $R_8$ is $CH_2$; E is S, SO, $SO_2$, $NR_{15}$ wherein $R_{16}$ is hydrogen or loweralkyl; $R_9$ is loweralkyl, cycloalkyl, cycloalkylalkyl, aryl, arylalkyl or an N-protected group, or E and $R_9$ taken together can be $N_3$, with the proviso that when E is NH, $R_9$ is an N-protecting group; and pharmaceutically acceptable salts thereof.

2. A compound as defined in claim 1 wherein $R_2$ and $R_4$ are hydrogen.

3. A compound as defined in claim 2 wherein $R_1$ is benzyl or 1- or 2-naphthylmethyl.

4. A compound as defined in claim 2 wherein $R_3$ is isobutyl or imidazole-4-yl-methyl.

5. A compound as defined in claim 2 wherein $R_5$ is cyclohexylmethyl.

6. A compound as defined in claim 2 wherein E is $SO_2$ or NH.

7. A compound as defined in claim 2 wherein $R_6$ is CO, $R_7$ is $CF_2$ and $R_8$ is $CH_2$.

8. A compound as defined in claim 7 wherein A is BocNH, $R_1$ is benzyl, $R_3$ is isobutyl, $R_5$ is cyclohexylmethyl.

9. A compound as defined in claim 8 wherein E is S and $R_9$ is isopropyl.

10. A compound as defined in claim 8 wherein E is $SO_2$ and $R_9$ is isopropyl.

11. A compound as defined in claim 8 wherein E and $R_9$ taken together are $N_3$.

12. A compound as defined in claim 2 wherein A is BocNH, $R_1$ is benzyl, $R_5$ is cyclohexylmethyl, $R_3$ is methyl, E is NH and $R_9$ is 4-methyl-pentanoyl.

13. A pharmaceutical composition for treating hypertension comprising a pharmaceutical carrier and a therapeutically effective amount of the compound of claim 1.

14. A method of treating hypertension comprising administering to a host in need of such treatment a therapeutically effective amount of the compound of claim 1.

* * * * *